(12) United States Patent
Helmer et al.

(10) Patent No.: US 7,126,041 B1
(45) Date of Patent: Oct. 24, 2006

(54) HIGH EFFICIENCY GENE TARGETING IN PLANTS

(75) Inventors: Georgia L. Helmer, Youngsville, NC (US); George C. Allen, Raleigh, NC (US); William F. Thompson, Raleigh, NC (US)

(73) Assignee: North Carolina State Unversity, Raleigh, NC (US)

( * ) Notice: Subject to any disclaimer, the term of this patent is extended or adjusted under 35 U.S.C. 154(b) by 847 days.

(21) Appl. No.: 09/733,869

(22) Filed: Dec. 8, 2000

Related U.S. Application Data

(60) Provisional application No. 60/170,069, filed on Dec. 10, 1999.

(51) Int. Cl.
*C12N 15/87* (2006.01)
*C12N 15/82* (2006.01)
*C12N 5/04* (2006.01)
*C12N 1/20* (2006.01)
*A01H 5/00* (2006.01)
*C07H 21/02* (2006.01)

(52) U.S. Cl. .............. 800/278; 800/294; 800/298; 800/300; 435/419; 435/468; 435/252.2; 435/320.1; 536/23.1

(58) Field of Classification Search .......... 435/468, 435/469, 440, 410; 536/23.1, 24.2
See application file for complete search history.

(56) References Cited

U.S. PATENT DOCUMENTS

| | | | |
|---|---|---|---|
| 5,527,695 A | 6/1996 | Hodges et al. | |
| 5,773,689 A | 6/1998 | Thompson et al. | |
| 5,773,695 A | 6/1998 | Thompson et al. | |
| 6,037,525 A | 3/2000 | Thompson et al. | |
| 6,100,448 A | 8/2000 | Thompson et al. | |
| 6,110,736 A | 8/2000 | Hodges et al. | |
| 6,187,994 B1* | 2/2001 | Baszczynski et al. | 800/278 |
| 6,239,328 B1 | 5/2001 | Thompson et al. | |
| 6,303,848 B1 | 10/2001 | Kumagai et al. | |
| 6,686,515 B1 | 2/2004 | Lassner et al. | |
| 6,746,870 B1* | 6/2004 | Ow et al. | 435/477 |
| 2004/0005713 A1* | 1/2004 | Baszczynski et al. | 435/469 |
| 2004/0016014 A1 | 1/2004 | Nguyen et al. | |
| 2004/0016015 A1 | 1/2004 | Nguyen et al. | |

FOREIGN PATENT DOCUMENTS

| | | |
|---|---|---|
| EP | 265556 | 5/1988 |
| WO | WO 97/41228 | 11/1997 |

OTHER PUBLICATIONS

Wei et al, Agrobacterium-mediated transformation: state of the art and future prospect, Chinese science Bulletin, vol. 45, No. 17, 2000, pp. 1537-1546.*
Copy of Specification of U.S. Appl. No. 09/733,397, filed Dec. 8, 2000, titled "High Efficiency Transformation in Plants Using a Site-Specific Recombinase" 52 pages.

* cited by examiner

*Primary Examiner*—Dave Trong Nguyen
*Assistant Examiner*—Maria Marvich
(74) *Attorney, Agent, or Firm*—Myers, Bigel, Sibley & Sajovec, P.A.

(57) ABSTRACT

The present invention provides a method for the targeted insertion of a nucleotide of interest into a specific chromosomal site within a plant cell. The method comprises the steps of: (a) providing a plant cell, the plant cell optionally but preferably having a heterologous target site on a chromosome thereof, wherein said target site is flanked by at least one recombination site; and then (b) transforming said plant cell with a transformation vector (e.g., with an *Agrobacterium* transformation vector) carrying a nucleotide sequence of interest, wherein said nucleotide sequence of interest is flanked by at least one recombination site that corresponds to the recombination sites of said target site, so that said nucleotide of interest is inserted into said chromosome at said target site (when a target site is employed).

7 Claims, 9 Drawing Sheets

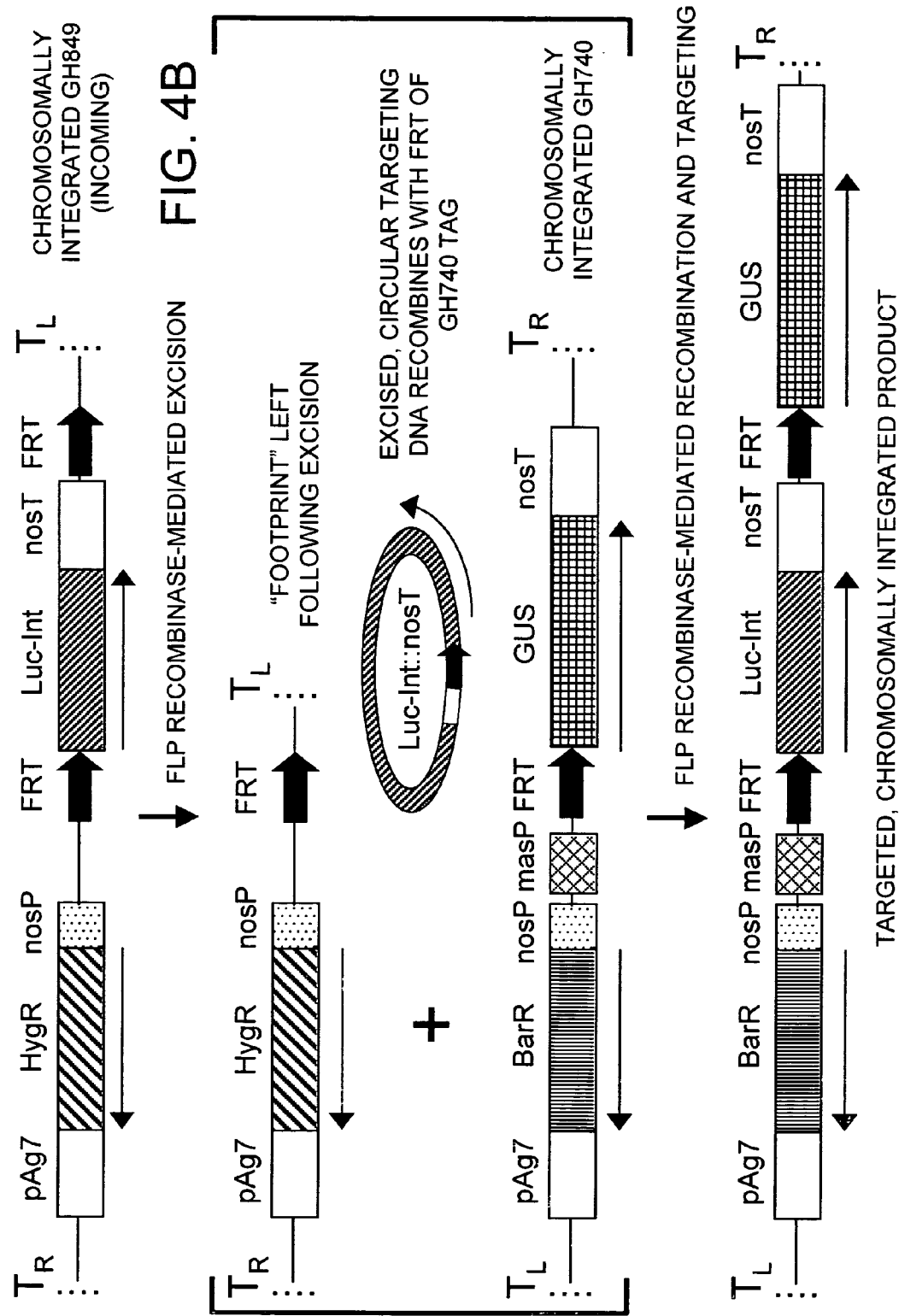

HIGH EFFICIENCY GENE TARGETING IN PLANTS

RELATED APPLICATIONS

This application claims the benefit of U.S. provisional application Ser. No. 60/170,069, filed Dec. 10, 1999, the disclosure of which is incorporated by reference herein in its entirety.

FIELD OF THE INVENTION

The present invention provides methods for the selective or targeted insertion of a heterologous nucleotide sequence of interest into the genome of, or the chromosomal DNA of, a plant cell, and the subsequent regeneration of plants from those transformed cells.

BACKGROUND OF THE INVENTION

It has now become common to insert heterologous DNA into plants, including both monocots and dicots. Vectors used to carry out such insertions, or "transform" the plants, include *Agrobacterium* vectors and ballistic vectors. Unfortunately, when plant transformations are routinely performed, the resulting transformants frequently express the transgene at unpredictable levels or at inappropriate times. And while it is true that plant transformation has become "routine", it is also true that plants vary widely with respect to their ability to be transformed, some plants being largely recalcitrant to transformation. For such difficult-to-transform plants therefore, it would be desirable to have higher efficiency transformation procedures and vectors, which are provided by the present invention.

The lack of predictability for expressing a genetic trait (for example, herbicide resistance) increases the cost of producing the desired plant because many "undesired" plants have to be initially screened to get the desired plant. The need to screen many transformants decreases the value of the transgenic crop and decreases confidence in the use of transgenic materials. Hence, it would be desirable to provide ways to introduce heterologous nucleic acids of interest into pre-established "target" sites within the genome of the plant to be transformed, where the DNA target site has been previously chosen to provide stable and predictable expression of the heterologous nucleic acid.

PCT Application WO99/25821 to Baszczynski et al. (assigned to Pioneer Hi-Bred) describes methods for the targeted excision of nucleotide sequences from a plant genome. P. Hooykaas describes the targeted delivery of a heterologous DNA by *Agrobacterium*-mediated transformation in *Arabidopsis* with the Cre/LOX site-specific recombination system (A. Vergunst et al., *Nucleic Acids Res.* 26, 2729 (1998); A. Vergunst and P. Hooykaas., *Plant Molec. Biol* 38, 393–406 (1998). However, high-efficiency targeted insertion of a desired nucleic acid into a plant of interest at a predetermined chromosomal site has not yet been described.

Transformation involves the insertion and integration of exogenous DNA into the genome of a cell by physical or biological means. True transformation in a precise and targeted manner, at a reasonably high efficiency, is a difficult, complex process. Accordingly, there is a continued a need in the art for such procedures.

SUMMARY OF THE INVENTION

The present invention provides a method for the targeted insertion of a nucleotide sequence of interest into a specific chromosomal site within a plant cell. The method comprises the steps of:

(a) providing a plant cell, the plant cell optionally but preferably having a heterologous target site on a chromosome thereof, wherein said chromosomal target site is a DNA sequence flanked by at least one recombination target site; and then (b) transforming said plant cell with a transformation vector (e.g., with an *Agrobacterium* transformation vector) carrying a nucleotide sequence of interest, wherein said nucleotide sequence of interest is flanked by at least one recombination target site that corresponds to the recombination target sites of said chromosomal target site, so that said nucleotide of interest is inserted into said chromosome at said chromosomal target site. Typically, the transforming step is be carried out in the presence of a site-specific recombinase effective to carry out recombination at said recombination target site and insert said nucleotide of interest into said chromosome at said recombination target site (when a recombination target site is employed), but this is not mandatory or essential in all cases.

Also disclosed herein is a method for the high efficiency insertion of a nucleotide of interest into a chromosome of a plant cell and regeneration of a plant from that cell without the need for an intervening selection step which exposes the transformed cells to toxic agents or the like. The method comprising the steps of:

(a) providing a population of plant cells, said target plant cells optionally but preferably having a heterologous target site on a chromosome thereof, wherein this chromosomal target site is flanked by at least one recombination target site; and then (b) transforming at least one of said population of plant cells with a transformation vector carrying a nucleotide sequence of interest, wherein said nucleotide sequence of interest is optionally but preferably flanked by at least one recombination target site that correspond to the recombination target sites of said chromosomal target site (if present) so that said nucleic acid of interest is inserted into said chromosome at said recombination target site; and then (c) isolating without selection a transformed plant cell from that population of plant cells; and then (d) regenerating a plant from said transformed plant cell.

As above, the transforming step may be carried out in the presence of a site-specific recombinase effective to carry out recombination at said recombination target site and insert said nucleotide of interest into said chromosome at said recombination target site.

The present invention is explained in greater detail in the drawings herein and the specification set forth below.

BRIEF DESCRIPTION OF THE DRAWINGS

FIG. 4B is a specific example of the general example of FIG. 4A for Flp/Frt-mediated site-specific recombination using screenable marker strategy. Plant chromosomal locus resulting from GH849 Agrobacterium infection; locus harbors a promotorless luc-int gene between direct repeats of the FRT site. GH849 confers Hygromycin resistance to plant cells. STEP 1: In the presence of Flp recombinase enzyme the circular DNA targeting intermediate "luc-int" is liberated from the T-DNA locus of GH849. This locus confers a HygR luc-minus phenotype. The HygromycinR "footprint" is left behind after excision. The GH740-"tagged" chromosomal locus confers a BarR GUS-Positive phenotype. STEP 2: In the presence of Flp recombinase, the Frt-luc-int circular intermediate recombines with the GH740 "tagged" chromosomal locus, producing the site-specific recombinant target integration (insertion) product indicated at bottom of diagram. This product is phenotypically BarR Luc-Positive GUS-Negative. TR, TL are T-DNA right and left borders respectively. nosP, masP are promoter regions of nopaline synthase and mannopine synthase genes, respectively. HygR, BarR, GUS are coding sequences for hygromycin phosphotransferase, bialaphos resistance gene, and beta-glucuronidase genes, respectively. luc-int is the firefly luciferase gene containing an intron. pAg7, nosT, are terminator sequences from Agrobacterium gene 7, and nopaline synthase gene, respectively.

DETAILED DESCRIPTION OF THE PREFERRED EMBODIMENTS

Figure 1:
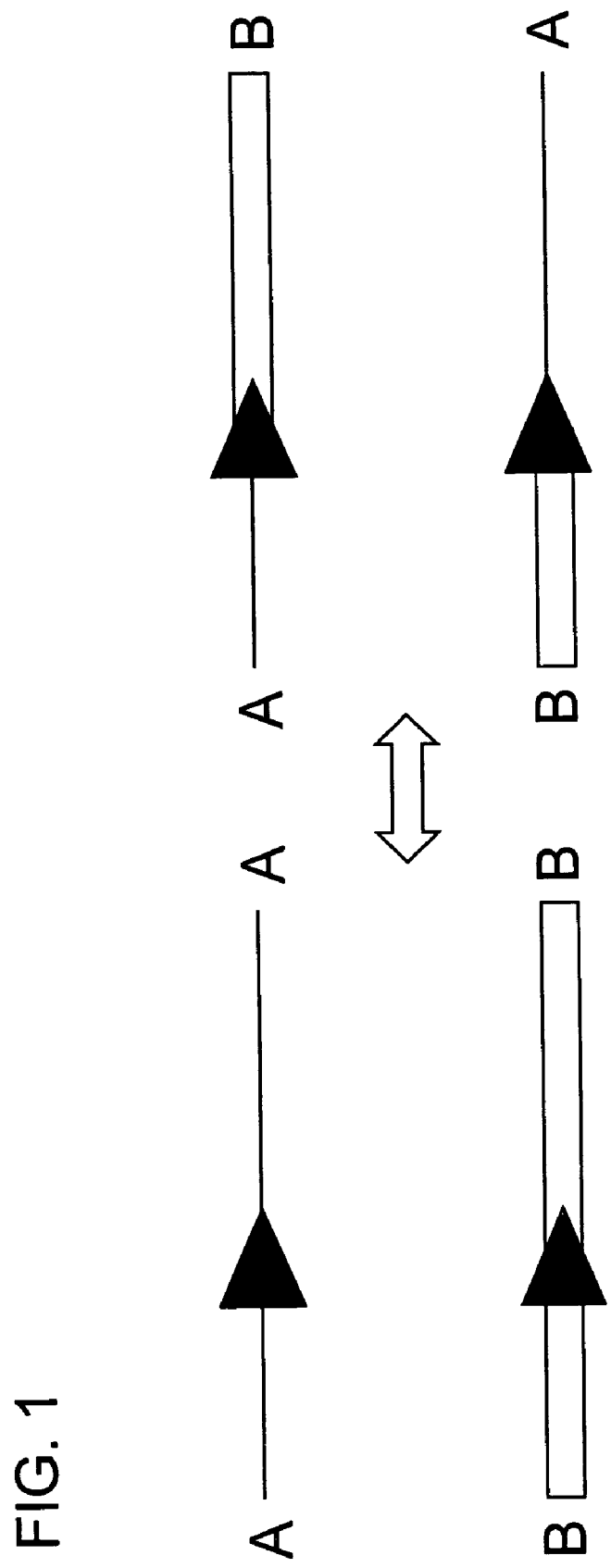
FIG. 1 is a schematic illustration of the method of the present invention, carried out with a single recombination target site flanking the chromosomal target site on DNA segment A and a single recombination target site flanking the incoming nucleic acid of interest on DNA segment B. The recombination target sites are indicated by the large solid arrows, each site being identical and oriented in the same direction with respect to each other. In the presence of the site-specific recombinase, a recombination between the two recombination target sites occurs resulting in a swap of DNA downstream of the sites, producing "hybrid" DNA molecules A-B and B-A.

The present invention provides methods for the high efficiency transformation of plants, and/or for high efficiency gene targeting in plants. The present invention may be embodied in a variety of different forms, which are summarized here and are explained in greater detail in the specification that follows.

Gene Targeting—Embodiment One—which requires all four components of the system in order to function for targeting: that is *Agrobacterium*, a heat-shock promoter, FLP recombinase, and at least one FRT (FLP recombinase target) site. It is further understood that FLP recombinase may be present as the DNA of the gene, as the mRNA, or as the protein. These four components function in such a way as to be necessary and sufficient for High Efficiency Gene Targeting.

Gene Targeting—Embodiment Two—which requires only three components of the system in order to function for targeting: that is that *Agrobacterium*, at least one FRT site and FLP recombinase. It is further understood that FLP recombinase may be present as the DNA of the gene, as the mRNA, or as the protein. These three components function in such a way as to be necessary and sufficient for High Efficiency Gene Targeting.

Gene Targeting—Embodiment Three—which requires only three components of the system in order to function for targeting: that is that a heat shock promoter, *Agrobacterium*, and at least one FRT site. These three components function in such a way as to be necessary and sufficient for High Efficiency Gene Targeting.

Gene Targeting—Embodiment Four—which requires only three components of the system in order to function for targeting: that is that a heat-shock promoter, at least one FRT site and FLP recombinase. It is further understood that FLP recombinase may be present as the DNA of the gene, as the mRNA, or as the protein. These three components function in such a way as to be necessary and sufficient for High Efficiency Gene Targeting.

Gene Targeting—Embodiment Five—which requires only three components of the system in order to function for targeting: that is that a heat-shock promoter, *Agrobacterium* and FLP recombinase. It is further understood that FLP recombinase may be present as the DNA of the gene, as the mRNA, or as the protein. These three components function in such a way as to be necessary and sufficient for High Efficiency Gene Targeting.

Gene Targeting—Embodiment Six—which requires only two components of the system in order to function for targeting: that is that *Agrobacterium* and at least one FRT site. These two components function in such a way as to be necessary and sufficient for High Efficiency Gene Targeting.

Gene Targeting—Embodiment Seven—which requires only two components of the system in order to function for targeting: that is FLP recombinase, and at least one FRT site. It is further understood that FLP recombinase may be present as the DNA of the gene, as the mRNA, or as the protein. These two components function in such a way as to be necessary and sufficient for High Efficiency Gene Targeting Gene Targeting—Embodiment Eight—which requires only two components of the system in order to function for targeting: that is FLP recombinase, and *Agrobacterium*. It is further understood that FLP recombinase may be present as the DNA of the gene, as the mRNA, or as the protein. These two components function in such a way as to be necessary and sufficient for High Efficiency Gene Targeting Gene Targeting—Embodiment Nine—which requires only two components of the system in order to function for targeting: that is FLP recombinase and a heat-shock promoter. It is further understood that FLP recombinase may be present as the DNA of the gene, as the mRNA, or as the protein. These two components function in such a way as to be necessary and sufficient for High Efficiency Gene Targeting.

Again, the recombinase may be present or provided through DNA in the target cell that expresses the recombinase, by the inclusion or introduction of mRNA into the target cell that expresses the recombinase, or by introduction of the recombinase protein itself into the target cell. In these embodiments, the transformation vector may employ a pair of flanking recombination target sites, or may employ a single flanking recombination target site. Further, in all these embodiments, the chromosomal or genomic DNA in the plant cell to be transformed may include a DNA target site having one or two flanking recombination target sites that correspond to the recombination target site, or may not include such a recombination target site.

Various aspects and embodiments of the present invention are explained in greater detail below.

A. Plants for Transformation.

The present invention may be used for transformation of any plant species, including both monocots and dicots. The present invention is particularly useful for the transformation of plants that have a complex or large genome. Thus, the present invention is particularly preferred for the transformation of plant species that have a genome greater than 500 megabases, or even greater than 1,000 or 2,000 megabases, in size.

In general, suitable plant species for transformation include, but are not limited to, corn (*Zea mays*), canola (*Brassica napus, Brassica rapa* ssp.), alfalfa (*Medicago sativa*), rice (*Oiyza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nuc-fera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mang-fera indica*), olive (*Olea europaea*), papaya (*Carica papaya*), cashew (*Anacardium occidentale*), macadamia (*Macadamia integnfolia*), almond (*Prunus amygdalus*), sugar beets (*Beta vulgaris*), oats, barley, vegetables, ornamentals, and conifers.

Vegetables include tomatoes (*Lycopersicon esculentwn*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caiyophyllus*), poinsettia (*Euphorbia puicherrima*), and chrysanthemum. Conifers which may be employed in practicing the present invention include, for example, pines such as loblolly pine (*Pinus taeda*), slash pine (*Pinus elliotif*), ponderosa pine (*Pinusponderosa*), lodgepole pine (*Pinus contorta*), and Monterey pine (*Pinus radiata*); Douglas-fir (*Pseudotsuga menziesii*); Western hemlock (*Tsuga anadensis*); Sitka spruce (*Picea glauca*); redwood (*Sequoiasempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, canola, soybean, cotton, peanut, sorghum, wheat, tobacco, etc.), more preferably corn and soybean plants, yet more preferably corn plants.

cleaved DNA of a second site. This reaction results in the precise recombination between two recombination target sequences. Such systems differ in complexity, varying in requirements for additional factors and in size of the DNA sites involved. For site-specific recombinases, such as FLP recombinase from yeast, the recombinase itself is in itself sufficient to catalyze recombination between specific target sites of 35-bp. FLP Recombinase Target (FRT) sites are comprised of 13-bp inverted repeat sequences (symmetry elements) flanking an 8-bp core region; these symmetry elements are where the recombinase binds. The recombinase target site core region is not involved in binding but is involved in crossing-over of the DNA sequences; the recombinase enzyme introduces single, staggered cuts near the ends of the core sequence. The asymmetry of the core gives directionality to the target sites, which can therefore align productively in only one orientation. For FLP, the minimal 35-bp FRT site is flanked by a third symmetry element; the "wild-type" site is therefore 48-bp. Scheme 1 shows the sequence, (SEQ ID NO: 9) the complementary strand (SEQ ID NO: 10) and structure of the FLP target site.

SCHEME 1

Sequence and structure of FLP recombination target site.

```
    FLP binding site           FLP binding site           FLP binding site
[13-bp symmetry element]  [13-bp symmetry element]  [13-bp symmetry element]
-----------y  core <-----------  <------------
GAAGTTCCTATACTTTCTAGAGAATAGGAACTTCGGAATAGGAACTTC
CTTCAAGGATATGAAAGAGAGATTATCCTTGAAGCCTTATCCTTGAAG
```

B. Site-Specific Recombination Systems.

Any site-specific recombination system, including the site-specific recombinase and corresponding recognition target sites that are specifically recognized by those recombinases, may be used in carrying out the present invention. Numerous such systems are known. See, e.g., J. Odell and S. Russell, *Use of Site-Specific Recombination Systems in Plants*, in Homologous Recombination and Gene Silencing in Plants, 219–270 (J. Paszkowski ed. 1994). In general, suitable recombinases include, but are not limited to integrases such as, FLP recombinase, Cre recombinase, and recombinase R. The recombination target sites are preferably ones bound and recognized by the recombinase, and include FRT in the FLP/FRT recombination system, Lox in the Crelox system, and R in the R/RS recombination system. See generally Schlake and Bode (1994) *Biochemistry* 33:12746–1275 1; Huang et al. (1991) *Nucleic Acids Research* 19:443–448; Bucholz et al. (1996) *Nucleic Acids Research* 24:3118–3119; Kilby et al. (1993) *Trends Genet.* 9:413–421: Rossant and Geagy (1995) *Nat. Med.* 1: 592–594; Albert et al. (1995) *The Plant J.* 7:649–659: Bayley et al. (1992) *Plant Mol Bid.* 18:353–361; Odell et al. (1990) *Mol. Gen. Genet.* 223:369–378; Dale and Ow (1991) *Proc. Nail. Acad. Sci. USA* 88:10558–105620); Albert et al. (1995) *Plant J.* 7:649–659; Qui et a). (1994) *Proc. Natl. Acad. Sd. USA* 91:1706–1710.

Recombinases are enzymes which cleave DNA at specific recombination target sequences and then ligate it to the "Gene targeting" can be distinguished from "targeting". Targeting reactions are those involving site-specific recombination target sequences and the related recombinase. "Gene targeting" is a special subset of "targeting" and has the very specific meaning that two pieces of DNA (not previously joined) have been cleaved by the FLP recombinase and relegated forming a new DNA junction. This cleavage and relegation occurs only at the appropriate recombination target sites (Flp Recombinase Target) sites and one of these sites is at a pre-determined site in the plant genome. This predetermined site in the plant genome is called the chromosomal target site.

In the examples given here, (see FIGS. 5 and 6 and Example 27) this new DNA junction formed is a 5' masP-FRT-luc-int 3' sequence, which has appeared nowhere else in the system. Also in our examples, a coding sequence (luciferase gene) is introduced on one side of the target; this simplifies detection of the desired product but is in no way a necessary component of the invention. The recombinase target site, FRT, is a substrate for the reaction of the invention but is not the invention. The recombination target site or pair of recombination target sites in the chromosomal target site can be identical or non-identical, and the pair of recombination target sites that flank the nucleotide sequence to be inserted can be identical or non-identical. Nonidentical recombination target sites different only in the sequence of the 8-bp core DNA. This sequence is mutated such that it can only align productively with an identical mutant target site;

thus it no longer is a substrate for recombination with the identical, or wild-type, sites. Where a single recombination target site is incorporated into the chromosomal target site, then that site is preferably positioned 5' to the insertion site.

The recombination target site or pair of recombination target sites in the chromosomal target site can be identical or non-identical, and the pair of recombination target sites that flank the nucleotide sequence to be inserted can be identical or non-identical. Nonidentical recombination target sites different only in the sequence of the 8-bp core DNA. This sequence is mutated such that it can only align productively with an identical mutant target site; thus it no longer is a substrate for recombination with the identical, or wild-type, sites. Where a single recombination target site is incorporated into the chromosomal target site, then that site is preferably positioned 5' to the insertion site.

The chromosomal DNA target site may be inserted into the chromosome of the target plant cells in accordance with known techniques, such as *Agrobacterium* transformation as described below, or ballistic transformation by bombardment of plant cells with microprojectiles that carry the DNA of interest, in accordance with known techniques. The presence of a promoter and a detectable gene such as gus in the chromosomal target site being inserted allows the pre-characterization of that target site. Further, the insertion a promoter 5' to the target site and 5' to the recombination target site in the chromosomal target site allows the inserted nucleic acid of interest to be regulated by that promoter. The present invention also allows use of a single chromosomal recombination target site in front of a promoterless gene to screen for new promoters or regulatory sequences.

Figure 2:
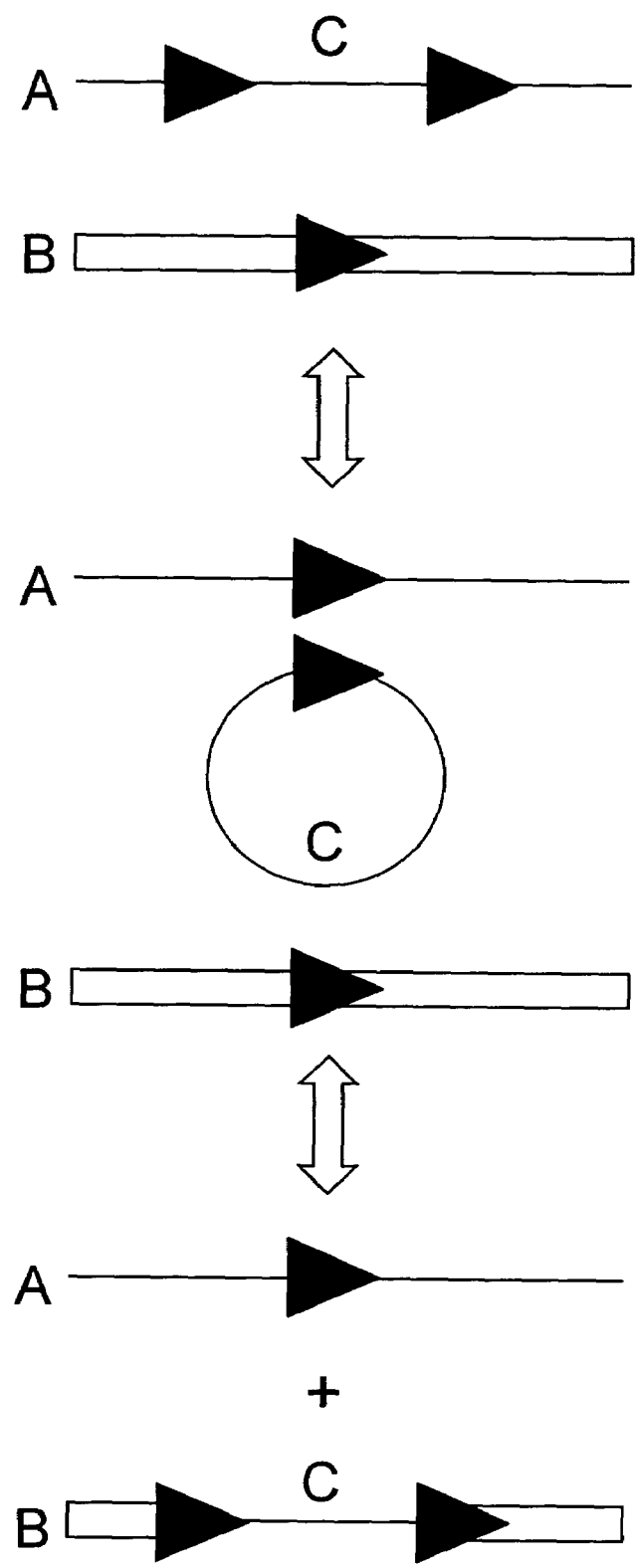
FIG. 2 is a schematic illustration of an alternate embodiment of the method of the present invention, carried out with a single recombination target site flanking the DNA target site on DNA segment B and a pair of recombination target sites flanking the incoming nucleic acid of interest on DNA segment A. The recombination target sites are indicated by the large solid arrows, each being identical and oriented in the same direction with respect to each other. In the presence of the site-specific recombinase, a recombination between two recombination target sites on DNA segment A occurs, resulting in excision and circularization of DNA sequence C. A second recombination event, between the recombination target site of circle C and the recombination target site on DNA segment B, results in the insertion of sequence C into sequence B at the recombination target site.
Figure 3:
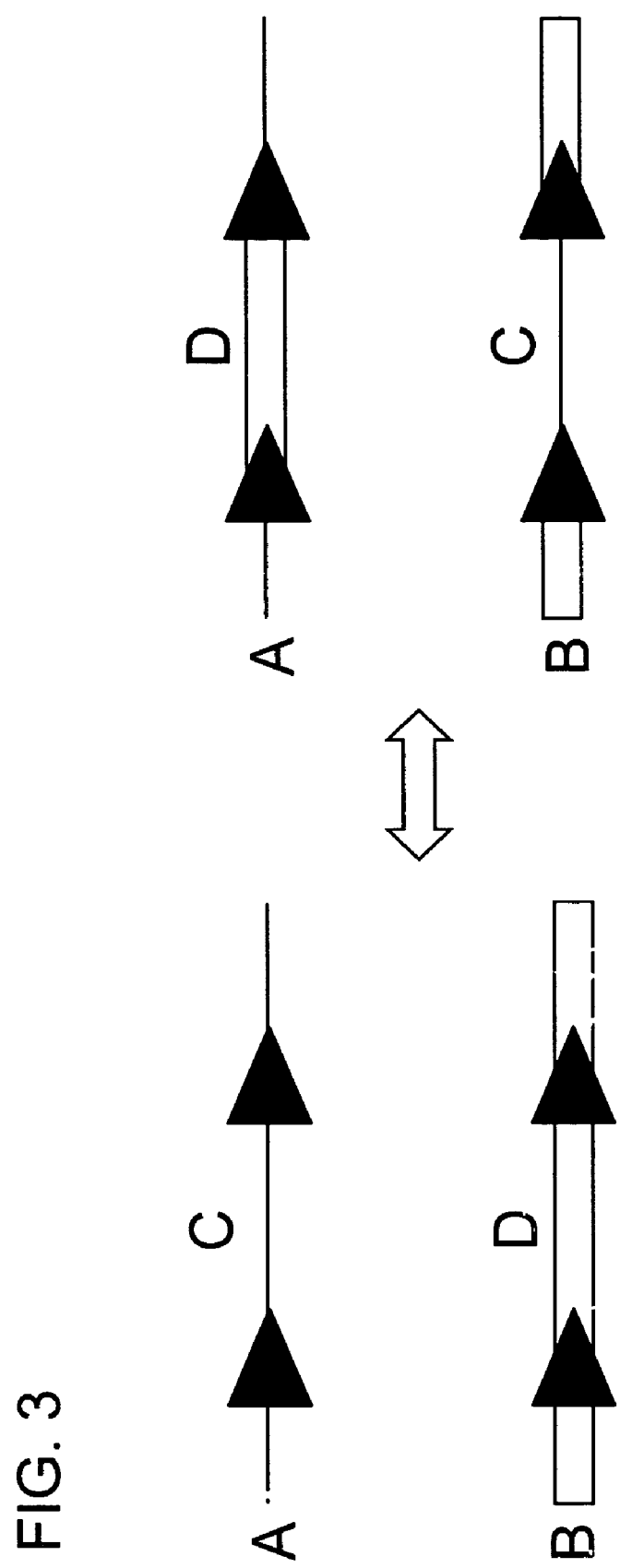
FIG. 3 is a schematic illustration of an alternate embodiment of the method of the present invention, carried out with a pair of recombination target sites flanking the target site C on DNA segment A and a pair of recombination target sites flanking the incoming nucleic acid of interest D on DNA segment B. The recombination target sites are indicated by the large solid arrows, each being identical and oriented in the same direction with respect to each other. In the presence of the site-specific recombinase, a recombination between recombination target sites on DNA segment A and DNA segment B occurs, resulting in DNA sequence C being replaced by DNA sequence D, and DNA sequence D being replaced by sequence C.
Figure 4A:
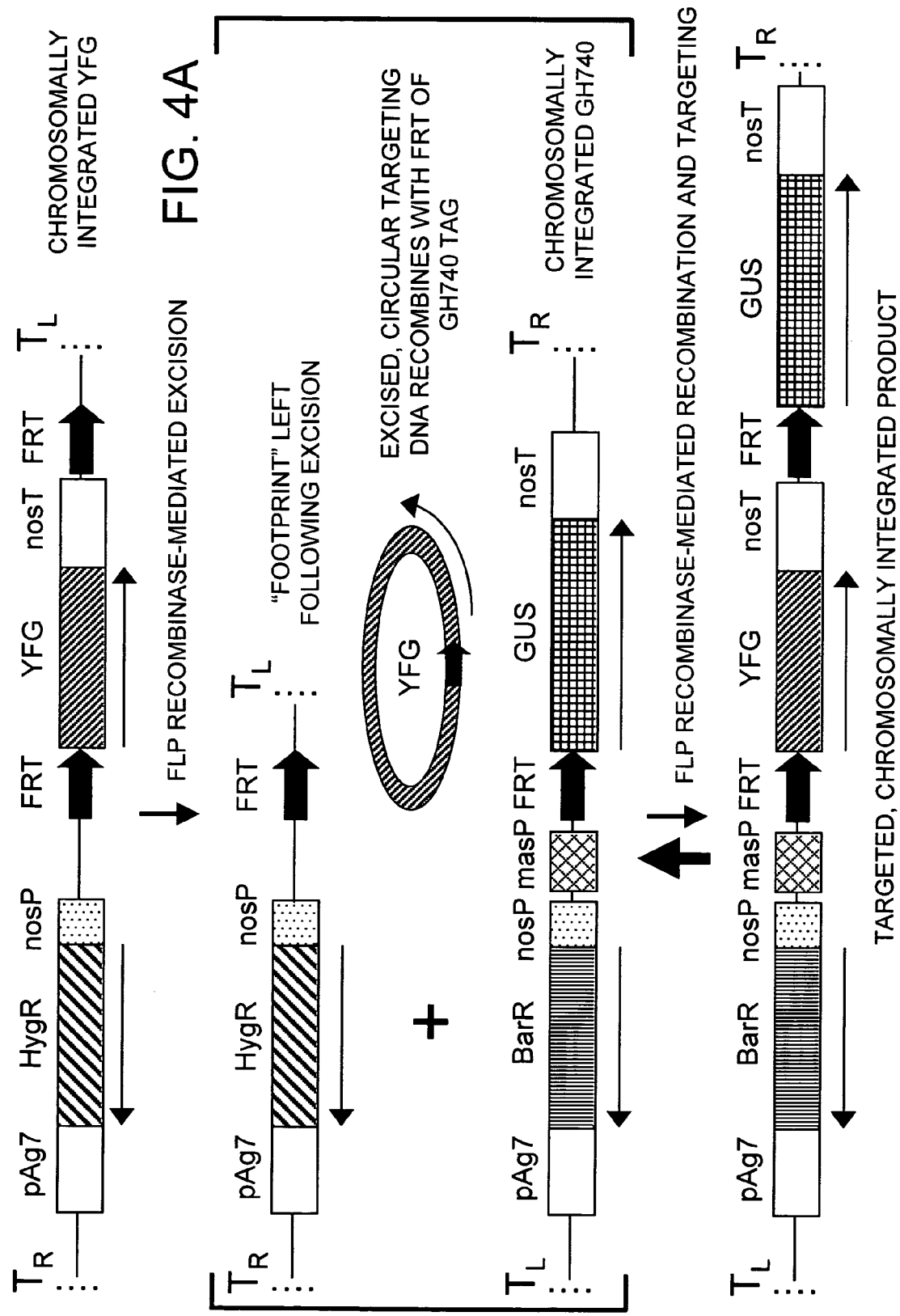
FIG. 4A is a schematic representation of a particular embodiment for Flp/Frt-mediated site-specific recombination of FIG. 3, which we term the Intragenomic Mobilization Strategy ("IMS"). The plant chromosomal locus resulting from T-DNA integration following Agrobacterium infection harbors a promotorless YFG (Your Favorite Gene) between direct repeats of the Frt recombination target sites. This construct confers Hygromycin resistance (for example) to plant cells. STEP 1: In the presence of Flp recombinase enzyme the circular DNA targeting intermediate "YFG" is liberated from the T-DNA locus having two FRT sites in direct repeat orientation The HygromycinR "footprint" is left behind after excision. The GH740-tagged chromosomal locus confers a BarR GUS-Positive phenotype. STEP 2: In the presence of Flp recombinase, the Frt-YFG circular intermediate recombines with the GH740-tagged chromosomal locus, producing the site-specific recombinant target integration (insertion) product indicated at bottom of diagram (Locus G). This product is phenotypically BarR YFG-Positive GUS-Negative.

The method of the present invention may be carried out with a single recombination target site flanking the chromosomal target site and a single recombination target site flanking the incoming nucleic acid of interest, as illustrated in FIG. 1. Alternatively, as illustrated in FIG. 2 the present invention, can be carried out with a single recombination target site flanking the chromosomal target site and a pair of recombination target sites flanking the incoming nucleic acid of interest. FIG. 3 illustrates the present invention carried out with a pair of recombination target sites flanking the chromosomal target site and a pair of recombination target sites flanking the nucleic acid of interest, and FIG. 4 illustrates a specific embodiment of FIG. 3 referred to as the Intragenomic Mobilization Strategy (or "IMS") for targeted integration. Of course, other combinations can be employed, such as a pair of recombination target sites on the incoming sequence with the nucleic acid of interest with a single recombination target site at the target site.

When the present invention is employed primarily for the purpose of high efficiency transformation, but targeted insertion is not required, then the presence of at least one recombination target site flanking the chromosomal target site is optional but preferable.

The transforming step is preferably carried out in the presence of a site-specific recombinase effective to carry out recombination at said recombination target site and insert the nucleotide of interest into said chromosome at said target site. Typically the recombinase is one that is known to correspond to the recombination target sites being employed. The recombinase may be administered by any suitable means, including by the administration of an exogenous protein, by the administration of RNA such as mRNA that encodes and expresses the recombinase, or by the administration of an expression cassette that expresses the recombinase in the target plant cells, which cassette may contain DNA encoding the recombinase under the control of a constituitively active promoter, or an inducible promoter such as a heat shock protein (hsp) promoter, and which expression cassette may be administered by any suitable means, such as by ballistic bombardment, electroporation, or *Agrobacterium*-mediated transformation.

The use of a Heat-shock promoter to regulate expression of the recombinase is of special interest. Heat-shock proteins (HSP) are induced at different temperatures in different organisms, but in each case induction occurs at a temperature that constitutes a stress for that particular organism. In plants the heat shock response occurs after an elevation of approximately 8–12 degrees C. above the normal growing temperature and is characterized by a very rapid induction of heat shock gene transcription. Although HSPs were initially defined as proteins whose expression is highly induced by elevated temperature, many recent studies indicate that these proteins are also regulated by a variety of environmental and developmental signals in animals and plants (Zimmerman and Cohill, 1991, *New Biologist* 3, 641–650). A number of reports have documented the expression or detection of low molecular weight HSP mRNAs in cases other than induction by heat stress (Waters et al, 1996, *J. Exper. Botany* 47, 325–338).

In the present invention, the Heat-shock promoter used, Gmhsp 17.6L, was not experimentally manipulated by inducing with heat stress. That had been the original experimental design. However, we realized upon observation of the cell lines that the Heat-shock promoter had been induced and the FLP recombinase expressed prior any experimental heat-shock manipulation by us.

C. Transformation Vectors.

In general, an expression vector comprises an expression cassette, the expression cassette comprising the DNA of interest. The DNA of interest may be operatively associated with a promoter on the expression cassette, or (for chromosomal targeted insertion as described herein) the promoter may be provided at the chromosomal target site so that the DNA of interest is operatively associated with that promoter upon integration into the target cell genome at the chromosomal target site. The vector may be embodied in any suitable form, such as an *Agrobacterium* vector (discussed below), a ballistic vector (where the DNA is carried into the desired target cell population on a ballistic vector by microparticle bombardment) or any other suitable technique.

*Agrobacterium* vectors. In a preferred embodiment of the present invention, plant cells are transformed using *Agrobacterium tumefaciens* or *Agrobacterium rhizogenes*, preferably *Agrobacterium tumefaciens*. *Agrobacterium*-mediated gene transfer exploits the natural ability of *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be removed by deletion of the genes in the T-DNA without loss of DNA transfer and integration. The DNA to be transferred is attached to border sequences, or T-DNA borders, that define the end points of an integrated T-DNA. One or both T-DNA borders are incorporated into the host chromosome in positions flanking the DNA of interest that has been inserted.

While the following discussion will focus on using *A. tumefaciens* to achieve gene transfer in plants, those skilled in the art will appreciate that this discussion applies equally well to *A. rhizogenes*. Transformation using *A. rhizogenes* has developed analogously to that of *A. tumefaciens* and has been successfully utilized to transform, for example, alfalfa, *Solanum nigrum* L., and poplar. U.S. Pat. No. 5,777,200 to Ryals et al. As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

The *Agrobacterium* strain utilized in the methods of the present invention is modified to contain a gene or genes of interest, or a nucleic acid to be expressed in the transformed cells. The nucleic acid to be transferred is incorporated into the T-region and is flanked by T-DNA border sequences. A variety of *Agrobacterium* strains are known in the art particularly for dicotyledon transformation. Such *Agrobacterium* can be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996), the disclosures of which are incorporated herein by reference.

In addition to the T-region, the Ti (or Ri) plasmid contains a vir region. The vir region is important for efficient transformation. Binary vector systems have been developed where the manipulated disarmed T-DNA carrying foreign DNA and the vir functions are present on separate plasmids. In this manner, a modified T-DNA region comprising foreign DNA (the nucleic acid to be transferred) is constructed in a small plasmid which replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

C58-derived vectors may be employed to transform *A. tumefaciens*. Alternately, in other embodiments, super-binary vectors are employed. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591,616, herein incorporated by reference) and pTOK233 (Komari, *Plant Cell Reports* 9,303 (1990); Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also typically contains an antibiotic resistance gene, a selectable marker gene, and the nucleic acid of interest to be transformed into the plant. The nucleic acid to be inserted into the plant genome is located between the two border sequences of the T region. Super-binary vectors of the invention can be constructed having the features described above for pTOK162. The T-region of the super-binary vectors and other vectors for use in the invention are constructed to have restriction sites for the insertion of the genes to be delivered. Alternatively, the DNA to be transformed can be inserted in the T-DNA region of the vector by utilizing in viva homologous recombination. See, Herrera-Esterella et al., *EMBO J.* 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Any suitable vector for transforming plants may be employed according to the present invention. For example, the heterologous nucleic acid sequence of interest and the flanking T-DNA can be carried by a binary vector lacking the vir region. The vir region is then provided on a disarmed Ti-plasmid or on a second binary plasmid. As another alternative, the heterologous nucleic acid sequence and the T-DNA border sequences can be put into the T-DNA site on the Ti-plasmid through a double recombination event by which the new T-DNA replaces the original Ti-plasmid T-DNA. The vir region can be supplied by the Ti-plasmid or on a binary plasmid. As yet a further alternative, the heterologous nucleic acid sequence and flanking T-DNA can be integrated into the bacterial chromosome as described by U.S. Pat. No. 4,940,838 to Schilperoort et al., and the vir region can then be supplied on a Ti-plasmid or on a binary plasmid.

The *Agrobacterium*-mediated transformation process of the present invention can be thought of as comprising several steps. The basic steps include an infection step and a co-cultivation step. In some embodiments, these steps are followed by a selection step, in other embodiments by a selection and a regeneration step and in even other embodiments by regeneration without selection.

An optional pre-culture step may be included prior to the infection step. The pre-culture step involves culturing the callus, frond, or other target tissue prior to the infection step on a suitable medium. The pre-culture period may vary from about 1 to 21 days, preferably 7 to 14 days. Such a pre-culture step was found to prevent transformation of maize cultures. See, e.g., EP 0 672 752.

In the infection step, the cells to be transformed are exposed to *Agrobacterium*. The cells are brought into contact with the *Agrobacterium*, typically in a liquid medium. As noted above, the *Agrobacterium* has been modified to contain a gene or nucleic acid of interest. The nucleic acid is inserted into the T-DNA region of the vector. General molecular biology techniques used in the invention are well-known by those of skill in the art. See, e.g., SAMBROOK ET AL., MOLECULAR CLONING: A LABORATORY MANUAL (1989).

*Agrobacterium* containing the plasmid of interest are preferably maintained on *Agrobacterium* master plates with stock frozen at about −80° C. Master plates can be used to inoculate agar plates to obtain *Agrobacterium* that is then resuspended in medium for use in the infection process. Alternatively, bacteria from the master plate can be used to inoculate broth cultures that are grown to logarithmic phase prior to transformation.

The concentration of *Agrobacterium* used in the infection step and co-cultivation step can affect the transformation frequency. Likewise, very high concentrations of *Agrobacterium* may damage the tissue to be transformed and result in a reduced callus response. Thus, the concentration of *Agrobacterium* useful in the methods of the invention may vary depending on the *Agrobacterium* strain utilized, the tissue being transformed, the plant species being transformed, and the like. To optimize the transformation protocol for a particular plant species or tissue, the tissue to be transformed can be incubated with various concentrations of *Agrobacterium*. Likewise, the level of marker gene expression and the transformation efficiency can be assessed for various *Agrobacterium* concentrations. While the concentration of *Agrobacterium* may vary, generally a concentration range of about $1\times10^3$ cfu/mL to about $1\times10^{10}$ cfu/mL is employed The tissue to be transformed is generally added to the *Agrobacterium* suspension in a liquid contact phase containing a concentration of *Agrobacterium* to optimize transformation efficiencies. The contact phase facilitates maximum contact of the tissue to be transformed with the suspension of *Agrobacterium*. Infection may be allowed to proceed for 1 to 30 minutes or more.

Those skilled in the art will appreciate that the conditions can be optimized to achieve the highest level of infection and transformation by *Agrobacterium*. For example, to enhance transformation efficiency, tissue may be cultured in medium containing an auxin, such as IAA, to promote cell proliferation (i.e., it is believed that *Agrobacterium* integrates into the genome during mitosis). As further alternatives, tissue wounding, vacuum pressure, or cultivation in medium containing acetosyringone can be employed to promote the transformation efficiency.

In the co-cultivation step, the cells to be transformed are co-cultivated with *Agrobacterium*. Typically, the co-cultivation takes place on a solid medium. Any suitable medium, such as Schenk and Hildebrandt medium (Schenk and Hildebrandt, *Can. J. Bot.* 50, 199 (1972)) containing 1% sucrose and 0.6% agar, may be utilized. The optimal co-cultivation time varies with the particular tissue. Tissue is co-cultivated with the *Agrobacterium* for about 2 to 7 days, preferably 2 to 5 days, more preferably 3 to 5 days, and more preferably 4 days. In contrast, callus is co-cultivated with the *Agrobacterium* for 0.5 to 4 days, more preferably 1 to 3 days, more preferably 2 days. Co-cultivation may be carried out in the dark or under subdued light conditions to enhance the transformation efficiency. Additionally, as described above for the inoculation step, co-culturing can be done on medium containing IAA or acetosyringone to promote transformation efficiency. Finally, the co-culturing step may be performed in the presence of cytokinins, which act to enhance cell proliferation.

D. Selection of Transformed Cells.

After the transformation step, the transformed tissue is typically exposed to selective pressure to select for those cells that have received the heterologous nucleic acid introduced by the expression cassette. The agent used to select for transformants will select for preferential growth of cells containing at least one selectable marker insert positioned within the expression cassette and delivered by the vector (or delivered with a separate, co-transformed, vector).

The conditions under which selection for transformants (from any tissue type or callus) is performed are generally the most critical aspect of the methods disclosed herein. The transformation process subjects the cells to stress, and the selection process can be toxic even to transformants. Typically, in response to this concern, the transformed tissue is initially subject to weak selection, utilizing low concentrations of the selection agent and subdued light (e.g., 1–5 $\mu$mol/m$^2$ sec, with a gradual increase in the applied selection gradient by increasing the concentration of the selection agent and/or increasing the light intensity. Selection pressure may be removed altogether for a time and then reapplied if the tissue looks stressed. Additionally, the transformed tissue may be given a "resting" period before any selection pressure is applied at all. The selection medium generally contains a simple carbohydrate, such as 1% to 3% sucrose, so that the cells do not carry out photosynthesis. In addition, the selection is initially performed under subdued light conditions, or even in complete darkness, so as to keep the metabolic activity of the cells at a relatively low level. Those skilled in the art will appreciate that the specific conditions under which selection is performed can be optimized for every species or strain of plant and for every tissue type being transformed without undue experimentation.

There is no particular time limit for the selection step. In general, selection will be carried out long enough to kill non-transformants and to allow transformed cells to proliferate at a similar rate to non-transformed cells in order to generate a sufficient callal mass prior to the regeneration step. Thus, the selection period will be longer with cells that proliferate at a slower rate. Type I plant callus, for example, proliferates relatively slowly and selection may be carried out for 8–10 weeks prior to regeneration.

E. Screening for Transformed Cells.

The screening procedures described above are, in general, disadvantageous in that the selective pressure can be toxic even to transformed plant cells. While strategies such as "resting periods" have been devised in an attempt to ameliorate this problem, such strategies make the procedure more lengthy and time consuming. It would be much preferable to be able to eliminate a selection step, but elimination of a selection step requires high transformation efficiencies to increase the number of positive transformants.

The methods of the present invention unexpectedly provide high transformation efficiencies. As a result, the selection step (involving the application of a selective pressure such as an antibiotic that provides preferential growth of transformed cells) can be eliminated in favor of a more benign screening step. Screening may be carried out without a selectable marker by using visual inspection such as by using a luciferase (luc) gene and visualizing luminescence from transformed cells after supplying the luciferin substrate, or by use of a biological marker such as a *Bacillus thuringiensis* protein that is expressed in transformed cells, detected with an antibody that specifically binds to the biological marker, or by PCR analysis to identify transformed cells carrying the DNA of interest. In any case, the need for applying a selective agent, antibiotic or the like in order to kill or inhibit the growth of nontransformed cells is obviated, making the overall procedure more rapid, and removing the need to expose transformed cells to a toxic agent.

F. Screening of Nucleic Acid Libraries in Plants.

The high efficiency transformation available through the methods of the present invention make them particularly useful in a method of screening a nucleic acid library in plant cells. Such libraries are, in general, genomic DNA libraries or cDNA libraries, or even synthetic libraries, which typically comprise at least 1000 different nucleic acids that are screened. In addition, such libraries may comprise a plurality of different nucleic acids that represent different combinations of "stacked" genes (e.g., different combinations of genes, or different orders of combinations of the same gene, such as from a putative genetic pathway). A library may be screened for a nucleic acid of interest from among the members of that library. A nucleic acid of interest is typically one that produces a detectable response, such as the expression of that nucleic acid (e.g., by screening the plant cells for a desired protein product), or the silencing (by any mechanism, including sense and antisense silencing, etc.) of a gene within that plant cell.

In general, the library screening technique comprises the steps of:

(a) providing a population of plant cells, said plant cells optionally but preferably having a heterologous chromosomal target site on a chromosome thereof, wherein that target site is flanked by at least one recombination site; and then (b) transforming a plurality of said plant cells with a plurality of transformation vectors, each of said transformation vectors carrying a different nucleic acid member of said library, wherein said nucleotide is flanked by at least one recombination target site that correspond to the recombination target sites of said chromosomal target site so that said nucleic acid is inserted into said chromosome at said target site to provide a plurality of different transformed plant cells; and then (c) screening said different transformed plant cells for said detectable response of interest.

The plant cells, recombination sites, vectors and transformation steps may be carried out as described above, with or without selection and/or screening after transformation as described above. Screening of the library in the cells may be carried out in accordance with known techniques, such as immunoassay for a gene product (both of a nucleic acid to be expressed and of a nucleic acid to be silenced), or by PCR analysis to determine presence of DNA. Screening may be carried out on plant cells as transformed, or on a tissue or even on plants regenerated from the transformed cells as described below and the screening step carried out on those tissue or plants. The transforming step is preferably carried out in the presence of a site-specific recombinase, as described above.

G. Regeneration of Plants from Transformed Cells.

Once transformed cells are selected or isolated by screening, plants are regenerated therefrom. Methods of regenerating certain plants from transformed cells are known in the art. See, e.g., Kamo et al., *Bot. Gaz.* 146, 327 (1985); West et al., *The Plant Cell* 5, 1361 (1993); and Duncan et al., *Planta* 165, 322 (1985 From plants derived from the transformed cells, pollen and seed can be collected therefrom and further progeny can be produced, all in accordance with known techniques.

During the regeneration process, any method known in the art may be utilized to verify that the regenerating plants are, in fact, transformed with the transferred nucleic acid of interest. For example, histochemical staining, visual imaging techniques such as photon imaging of luciferase activity, ELISA assay, Southern hybridization, northern hybridization, western hybridization, PCR, and the like can be used to detect the transferred nucleic acids or protein in the callus tissue and regenerating plants.

Now that it has been demonstrated that plants can be transformed utilizing ballistic bombardment and *Agrobacterium*, alterations to the general methods described herein can be used to increase efficiency or to transform strains that may exhibit some recalcitrance to transformation. Factors that affect the efficiency of transformation include the species of plant, the tissue infected, composition of the media for tissue culture, selectable marker genes, the length of any of the above-described step, kinds of vectors, temperature, and light/dark conditions. Specifically for *Agrobacterium*-mediated transformation, the concentration and strain of *A. tumefaciens* or *A. rhizogenes* must also be considered. Therefore, these and other factors may be varied to determine what is an optimal transformation protocol for any particular plant species or strain. It is recognized that not every species and strain will react the same way to the transformation conditions, and each species and strain may require a slightly different modification of the protocols disclosed herein. However, by altering each of the variables, an optimum protocol can be derived for any plant line.

The present invention is explained in greater detail in the following non-limiting Examples. The inducable Heat Shock Flp, designated HSP FLP, was the gift of J. A. H. Murray and is made in accordance with known techniques. (Kilby, N. J. et al, *Plant Journal* 8 (5):637–652 (1995). This contains the Gmhsp17.6L soybean heat-shock promoter (Severin, K and Schoffl, F. (1990) *Plant Mol. Biol.* 15:827–833). *Agrobacterium tumefaciens* LBA 4404 (Gibco BRL) was used in all cell and plant transformation. Commercially available biologicals and kits were used in accordance with the manufacturer's directions. All molecular biology protocols unless indicated otherwise are as described in *Current Protocols in Molecular Biology*, ed. L. M. Albright, D. M. Coen, & A. Varki, John Wiley & Sons, New York, 1995. or *Molecular Cloning, A Laboratory Manual*, 2nd edition, 1989, by J. Sambrook, E. F. Fritsch, & T. Maniatis; Cold Spring Harbor Laboratory Press, Cold Spring Harbor, N.Y.

EXAMPLE 1

Initial Findings

In this experiment tobacco plant cell lines were transgenic for (a) HSP FLP (the FLP recombinase gene under control of the Gmhsp17.6L promoter), (b) a chromosomal "tag" genetic sequence that contained an FRT (Flp Recombinase Target) site situated between a promoter and a coding sequence plus terminator with the FRT recombination target site situated 5' of the coding sequence (in the experiment described the Tag coding sequence was a GUS reporter gene); and (c) an incoming DNA sequence comprising a second (different) coding sequence plus terminator flanked by FRT recombination target sites in direct repeat orientation; this incoming DNA was the "incoming targeting gene" and for the experiment described, the incoming targeting gene was a luciferase (luc) gene. The starting point was cell lines into which elements (a) and (b) had been stably transformed via *Agrobacterium*. The incoming DNA (c) was then introduced and the following surprising results were found.

The experiment involved the use of a host tobacco cell line that contained a chromosomal Tag site (the FRT from the yeast 2 micron plasmid) between a modified mannopine synthase promoter and a GUS reporter. The chromosomally-tagged plant cell also contained the Flp recombinase gene (a site-specific recombination enzyme that can catalyze the recombination between FRT sites) that could be activated by heat shock (the Flp gene contains the soybean heat shock promoter); this had been separately introduced. The chromosomal Tagged cells were then re-transformed with an *Agrobacterium* vector bearing a promoterless luciferase reporter with an FRT site so situated that site-specific recombination would position the luciferase gene next to the chromosomal Tag promoter resulting in luciferase gene activation.

Approximately 20 Tagged cell lines were independently transformed with the promoterless luciferase gene. These were then heat-shocked to activate the recombination (and hopefully the targeting reaction). The luciferase activity of the heat-shocked cells was then visualized by providing 5 mM luciferin substrate and imaging with the Hamamatsu photon imager. The hope was to see small areas of microcalli that were emitting light, which would be the expected phenotype for successful targeting at the low frequency expected.

All or most of the cells on the filter were emitting light. The culture that had not been heat-shocked was then checked. All (or many) of the calli were emitting light. Clearly, if this were targeting, it had to have occurred before or in the absence of the heat shock treatment. It may have been that *Agrobacterium* could activate the soybean heat shock promoter, or that targeting could occur in the presence of low levels of Flp that might result from leaky expression of an "uninduced" heat shock promoter. Regardless, the phenotype that was observed was clearly one in which targeting had occurred.

All (16) of the Tagged GH849 (promoterless luciferase, flanked with FRT sites) cell lines for luciferase were screened and all express luciferase at varying levels.

EXAMPLE 2

Synthesis of FRT Sites

Flp Recombinase Target (FRT) sites were synthesized as complementary oligonucleotides and annealed. Two FRT sites were constructed differing only in the restriction endonuclease sites added at either end. The forward (5'-3') oligonucleotide sequence for the 5' FRT was 5'-FRT: XhoI-5'-FRT-SalI, as follows: CGACTCTCGAGGAAGTTC-CTATTCCGAAGTTCCTATTCTCTAG (SEQ ID NO:1);

The antisense oligonucleotide for the 5' FRT sequence for the 5'-FRT: XhoI-5'-FRT-SalI was: CAGATGTCGAC-GAAGTTCCTATACTTTCTAGAGAATAGGAAC (SEQ ID NO:2).

The forward (5'-3') oligonucleotide sequence for the 3' FRT was 3'-FRT: BamHI-3'-FRT-KpnI, as follows: CGACTGGATCCGAAGTTCCTATTCCGAA GTTCCTATTCTCTAG (SEQ ID NO:3).

The antisense oligonucleotide sequence for the 3' FRT was 3'-FRT: BamHI-3'-FRT-KpnI, as follows: CAGAGG-TACCGAAGTTCCTATACTTTCTAGAGAATAGGAAC (SEQ ID NO:4).

Each set of oligonucleotides was designed to be complimentary one to the other such that upon annealing a double-stranded molecule with 5' overhangs resulted. In the sequences above, the overlap sequences are underlined and printed in bold type. The overlap in each case produced a 15-bp double-strand.

Each sticky-ended duplex was filled in using T-4 DNA polymerase (New England Biolabs) at 11° C. to produce fully, double-stranded DNA. The double-stranded DNA fragments were identified and purified using polyacrylamide gel electrophoresis.

EXAMPLE 3

Cloning the FRT Sites

The 5'FRT: The FRTs were then directionally cloned using a stepwise procedure which took advantage of the fact that the FRT sequence had a unique internal XbaI site; the 5'FRT duplex was cut with XhoI+XbaI and ligated into the vector pSL301 (InVitrogen) cut with the same enzymes. The resulting product was cut with XbaI+SalI and the XbaI+SalI fragment of the 5'FRT duplex ligated in, producing pSL301-5'FRT.

The 3'FRT: 3'FRT was cloned by cutting the 3' FRT duplex with BamHI+XbaI and inserting it into BamHI/XbaI cut pSL301. The ligation product from this was then cut with XbaI+KpnI and the XbaI+KpnI fragment from 3'FRT inserted. The 3'FRT BamHI/KpnI fragment was gel isolated and inserted into BamHI/KpnI cut pSL301-5'FRT, producing pSL301-5'FRT-multiple cloning site-3'FRT.

The Mannopine Synthase Promoter (mas)—A unidirectional mas promoter was constructed using PCR amplification of pAGM139 (Gerry Hall, Mycogen) as template and the sense strand oligo: GCGCACGCGTAAGCTTA-GATTTTTCAAATCAGTGCGC (SEQ ID NO:5), which added MluI and HindIII sites 5', and an antisense strand oligo: GCGCATGCATTCTAGACGATTTGGTG-TATCGAGATTGG (SEQ ID NO:6), which added Nsi and XbaI sites 3'. The product resulting from this was cut with HindIII+XbaI and the resulting gel-purified fragment ligated into pSL301 cut with HindIII+SpeI. The resulting product retained the HindIII site but had the SpeI site destroyed. This mas promoter corresponds to the 318-bp piece from the mas gene described by Ni et al ((1996) *Plant Mol. Biol.* 30, 77–96).

EXAMPLE 4

Plasmid GH 700

The plasmid Omega GUS (Lynn Dickey, Biolex, Raleigh N.C. and Gallie et al., *Plant Cell* 1, 301–311 (1989)) was cut with XbaI and treated with Klenow to blunt-end the XbaI site. The resulting linear piece was cut with EcoRI, producing a 2-kb fragment. This was ligated into pGH355 cut with NruI and EcoRI producing pGH 669, which had the insert <nosP/Frt/omega-gus/nosT>. Plasmid pGH700, having the insert <masP/Frt/omega-gus/nosT>, was generated by ligating HindIII+SpeI cut pGH669 and the ~350-bp mas promoter PCR fragment cut with HindIII and XbaI.

EXAMPLE 5

Construction of Plasmid pGH740: The Chromosomal Tagging Construct

A 2.3-kb HindIII/EcoRI fragment was liberated from pGH700 and ligated into the binary plasmid pGPTV-BAR (Becker et al, *Plant Molecular Biology* 20:1195–1197 (1992)) cut with EcoRI+HindIII. This produced pGH740, the Tagging Construct; having the insert <masP/Frt/omega-gus/nosT>.

EXAMPLE 5A

Construction of Plasmid pGH850

The Incoming Integration Construct Containing a Single FRT Site

The pGH850 construct contained the insert <5'FRT-luc-int-nosT> cloned into the EcoRI and HindIII sites of plasmid BinHygTX (D. Becker, *Nucleic Acids Research* 18:203 (1991)). This insert resulted from a fortuitous in vivo deletion of masP sequences in a construct originally bearing <masP-5'FRT-luc-int-nosT>.

EXAMPLE 6

Construction of Plasmid pGH849

The Incoming Targeting Construct Containing Two FRT Sites

Plasmid pGH845 was cut with HindIII+EcoRI and the resulting 2.2-kb fragment isolated. This was then ligated into the large fragment of the plasmid Bin-Hyg-TX (D. Becker, *Nucleic Acids Research* 18: 203 (1991)) cut with EcoRI and HindIII. The resulting binary plasmid was pGH849 which had the incoming targeting sequence, <5'FRT/luc-int/nosT/3'FRT>.

EXAMPLE 7

Construction of Plasmid pGH845

Plasmid pGH845 was constructed by cutting pGH835 with BglII and MfeI, isolating the large backbone fragment, and ligating in the 2.2-kb BamHI/EcoRI luc-int gene-containing fragment from plasmid pLuk07. In this process both the BamHI and EcoRI sites were destroyed.

pLuk07 was constructed by Luke Mankin in accordance with known techniques. (*Plant Molecular Biology Reporter* 15:186–196 (1997)).

EXAMPLE 8

Construction of Plasmid pGH835

Plasmid pGH835 (<5'FRT-mcs-3'FRT>) was constructed by cutting pMS101 (Snaith, M. R. et al, *Gene* 166:173–174 (1995)) with BglII and EcoRI and isolating the large backbone fragment. Into this was ligated the ~100-bp BglII/EcoRI fragment from pGH288. Plasmid pMS101 had the multiple cloning site of pSL1180.

EXAMPLE 9

Construction of Plasmid pGH288

Plasmid pGH288 was constructed by cutting pGH220 with BamHI and SalI and isolating the large backbone fragment. Into this was ligated the 215-bp XhoI/BamHI fragment of the multiple cloning site of pSL301 (InVitrogen). Both the SalI and the XhoI sites were eliminated in this process.

EXAMPLE 10

Construction of Plasmid pGH220

The plasmid pGH220 was constructed by cutting pGH130 with SalI and BamHI, isolating the large backbone fragment, and inserting the 1.7-kb SalI/BamHI fragment from pPluc (Bonin, A. L. et al, (1994) *Gene* 141:75–77).

EXAMPLE 11

Construction of Plasmid pGH130

Plasmid pGH130 was constructed by the following steps:

(a) Cutting pSL301 (InVitrogen) with HindIII and SpeI, isolating the large fragment, and ligating into it a ~300-bp HindIII-SpeI nos (nopaline synthase) promoter fragment generated by PCR amplification.

(b) Cutting the product from (a) with XhoI and SalI and ligating in the XhoI-5'FRT-SalI described above (Example 2). This produced <nosP/5'FRT>.

(c) Cutting the product from (b) with HindIII and SalI and isolating the ~400-bp nosP-5'FRT fragment. Ligating this fragment into plasmid pJKK/luxF (Kirshman J A and J H Cramer, Gene 68:63–165 (1988)) cut with HindIII and SalI. The resulting plasmid was pGH105.

(d) Cutting pGH105 with BamHI and KpnI, isolating the large backbone fragment, and ligating into it the BamHI-3'FRT-KpnI described above (Example 2) to produce pGH130.

EXAMPLE 12

Construction of Plasmid pGH304

A 1.5-kb BglII/XhoI fragment, containing the Flp recombinase coding sequence, was isolated from pOG44 (Stratagene) and ligated into pSL301 cut with BglII and XhoI to produce pGH304.

EXAMPLE 13

Construction of Plasmid pGH855

Plasmid pLuk07 was cut with BamHI and EcoRI and the 2.2-kb luc-int BamHI/EcoRI fragment was isolated. This fragment was ligated into the large backbone fragment of pGH700, cut with BamHI and EcoRI, to produce the Positive Control having the insert <masP/Frt/luc-int/nosT>.

EXAMPLE 14

Making Electrocompetent Agrobacterium

The following procedure was used to make electrocompetent Agrobacterium cells:

1. Wild-type Agrobacterium cultures were grown overnight at 29° C. in 5 mL YEB.
2. 100 mL of YEB medium (500 mL flask) was inoculated with 2.5 mL of the overnight culture.
3. Cultures were incubated at 29° C. until the OD600 was 0.5–0.7.
4. Cells were put on ice for 10 minutes and kept as cold as possible for the remainder of the protocol.
5. Cells were pelleted by centrifugation at 8000 rpm for 10 min at 4° C. Subsequently, the supernatant was poured off and the pellet was returned to ice.
6. Cells were resuspended in 10 mL of ICE COLD, sterile 10% glycerol by vortexing vigorously. Subsequently, cells were pelleted at 8000 rpm for 5 min at 4° C.
7. Step #6 was repeated for a total of 4 washes.
8. Cells were resuspended in 1 mL of ICE COLD, sterile 10% glycerol by vortexing vigorously. Cells were aliquoted quickly into microfuge tubes and frozen in liquid nitrogen.
9. Cells were stored at −70° C. until used.

EXAMPLE 15

Agrobacterium Electrotransformation

The following procedure was used to carry out electrotransformation with Agrobacterium cells.

1. Electrocompetent cells were thawed on ice.
2. 40 µL of electrocompetent cells were added to an ICE COLD, sterile BioRad Gene Pulser cuvette (Gap=0.2 cm). Then, 2 µL DNA solution was added to the electrocompetent cells. The cells and DNA were flicked to the bottom of the cuvette.
3. The outside of the cuvette was dried and the cuvette was placed into the Gene Pulser chamber. Cells were electroporated at 2.50 kV, 25° C., and 600 µF.
4. Immediately, 1 mL of ICE COLD YEB was added and the cuvette was returned to the ice.
5. Once all electroporations were completed, the Agrobacterium was allowed to recover at 29° C. for 1–3 hours with gently shaking
6. After recover the Agrobacterium was plated on selective medium and allowed to grow for 2 days until colonies began to appear.

EXAMPLE 16

Agrobacterium Plasmid Miniprep

The following procedure was used to isolate plasmid DNA from Agrobacterium cells.

1. A spatula of lysozyme for each mL of Qiagen™ P1 miniprep reagent was prepared.
2. Agrobacterium cells pelleted, resuspended in 250 µL of the P1+ lysozyme solution from (1), and incubated at room temperature for 5 min.
3. 250 µL of Qiagen™ P2 reagent was subsequently added and the resulting solution was mixed by gentle inversion. The mixture was incubated at room temperature for 5 min.
4. 350 µL of Qiagen™ N3 reagent (Qiaspin Reagent) was subsequently added and the resulting solution was immediately mixed by gentle inversion.
5. The lysed cells were centrifuged at more than 13,000 rpm for 15 min resulting in a slimy, slug-like pellet at the bottom of the tube.
6. The supernatant was removed and transferred to a Qiagen™ spin column. The spin column was centrifuged for 30 sec at 13,000 rpm and the effluent was discarded.
7. The column was subsequently washed with 500 µL of Qiagen™ PB reagent, centrifuged for 30 sec at 13,000 rpm, and the effluent discarded.
8. The column was next washed with 750 µL of Qiagen™ PE reagent, centrifuged for 30 sec at 13,000 rpm, and the effluent discarded.
9. The column was again centrifuged for 30 sec at 13,000 rpm and the effluent discarded.
10. The DNA was eluted from the column with 50 µL of ~70° C. sterile H$_2$O.

EXAMPLE 17

Growth and Culture of NT-1 Tobacco Cell Lines

The *Nicotiana tabacum* cell line NT-1 was originally obtained from G. An, Washington State University, Pullman, Wash. and cultured in the laboratory for ten years. Suspension cultures were grown in a medium containing Murashige and Skoog salts (GIBCO Laboratories, Grand Island, N.Y.) supplemented with 100 mg/L inositol, 1 mg/L thiamine HCl, 180 mg/L $KH_2PO_4$, 30 g/L sucrose, and 2 mg/L 2,4-D. The pH was adjusted to 5.7 before autoclaving. Cells were subcultured once per week by adding 3 mL of inoculum to 100 mL of fresh medium in 500 mL Erlenmeyer flasks. The flasks were placed on a rotary shaker at 125 rpm and 27° C. with a light intensity of 47 mmol m−2 sec−1.

EXAMPLE 18

Transformation of NT-1 Tobacco Cell Lines

For all *Agrobacterium* transformations, 4.0 mL of four-day-old NT-1 cells were mixed with 100 μL of *Agrobacterium* containing the various T-DNA vectors. The *Agrobacterium* and NT-1 cell mixture was incubated for 48 hours at 27° C., after which the mixture was diluted and plated out on solid NT-1 medium containing an antibiotic (timetin), to kill the *Agrobacterium*, plus a plant selective antibiotic or herbicide. Isolated antibiotic- or herbicide-resistant microcalli began to appear in approximately 2–3 weeks, at which time they were transferred to fresh plates containing the appropriate antibiotic or herbicide in NT-1 medium. After 7–10 days growth on plates, a suspension culture was started for each callus by inoculating 1 mL of broth supplemented with the appropriate antibiotic or herbicide. Once established, the suspension cultures were transferred weekly using 3% (v/v) inocula in 5 mL of broth supplemented with the appropriate antibiotic or herbicide.

EXAMPLE 19

Tobacco Leaf Discs: Infecting with *Agrobacterium*

Tobacco leaves were surface sterilized with 95% v/v EtOH and 50% v/v Clorox bleach (equivalent to 2.6% w/v sodium hypochlorite), then washed four times in sterile distilled water. Leaf discs were cut aseptically then dipped into a 48 hour culture of the appropriate *Agrobacteria*, and plated onto 0.8% w/v Phytagar (Gibco BRL) containing OSMTob medium (Horsch, R. B., J. E. Fry, N. L. Hoffmann, D. Eichholtz, S. G. Rogers, and R. T. Fraley, *Science* 227:1229–1231. (1985)) lacking any antibiotics. After 2–3 days, leaf disks were transferred to OSMTob plates containing timetin, to kill the *Agrobacteria*, plus the appropriate antibiotic to select for transformed plant cells.

EXAMPLE 20

Heat Shock Manipulation of NT-1 Cell Lines

NT-1 tobacco lines, containing transgenes HspFLP and GH740, were transformed with *Agrobacterium* bearing pGH849. Independently-transformed cell lines were then inoculated into 5 mL of NT-1 liquid containing 50 μg/mL hygromycinB (ICN Biomedical, Aurora, Ohio). Cultures were grown in constant light at 27° C. at 125 rpm shaking and transferred weekly (1:10::v:v).

The heat shock experiment was done as follows:

(a) 0.5 mL of 7-day old cells were inoculated into 4.5 mL fresh medium.

(b) The remaining cells (4.5 mL) were then heat-shocked at 40° C. for 120 minutes while shaking at 125 rpm.

(c) The heat-shocked culture was then inoculated (0.5 mL) into 4.5 mL fresh medium containing 50 μg/mL hygromycin B at 27° C. for culture maintenance (+HS).

(d) The remainder of the heat-shocked culture was diluted 1:1 with fresh medium (4.5 mL→9 mL) and 1.0 mL aliquots plated onto sterile paper circles atop fresh NT-1 solid medium in 60 mm culture dishes. Each heat-shocked sample yielded nine 1.0 mL samples.

(e) Plated samples were then returned to the growth incubator and allowed to grow for 48 hours prior to further analysis.

EXAMPLE 21

Luciferase Imaging

Luminescence was measured with a Hamamatasu Argus-50 PCC Photon Imager immediately after the addition of the desired amount (usually 50–100 μL) of 5 mM D-luciferin (Biosynth). The Hamamatasu Argus-50 settings were 5 to 10 V for one to 75 minutes.

EXAMPLE 22

Histochemical GUS Assay

GUS activity in plant tissue was visualized by histochemical staining with 5-bromo-4-chloro-3-indoyl-beta-D-glucuronic acid (X-Gluc, Biosynth) as described (Jefferson, R. A., *Plant Mol. Biol. Rep.* 5:387–405 (1987)). Tissue was incubated at 37° C. for 24 hours, then destained using 95% EtOH.

EXAMPLE 23

Nuclear DNA Isolation

Nuclear DNA was isolated as described previously (Allen, et al, *Plant Cell* 5:603–613; (1993)) by filtering 5 mL suspension cell culture through Whatman Paper and scraping the dried samples into Falcon tubes and snap freezing in liquid nitrogen for storage at −70° C. The samples were ground under liquid nitrogen in a pre-cooled (−70° C.) mortar. Subsequently, 10 mL pre-cooled Nuclei Isolation Buffer (NIB1) per sample was added. NIB1 contains 3% β-mercaptoethanol, 5.9% hexylene glycol, 1% thiodiglycol, 20 mM KCl, 20 mM HEPES (pH 7.4), 0.5% Triton X-100, 0.5 mM NaEDTA (pH 7.4), 0.05 mM spermine, and 0.125 mM spermidine. The suspension was then centrifuged at 500×g in a swinging bucket centrifuge and the pellet was resuspended into 1 mL Nuclei Isolation Buffer (NIB1) kept at 4° C. One mL of 2× Lysis Buffer which contains 0.2M Tris (pH 8.0), 50 mM NaEDTA, 1M NaCl, and 2% Sarkosyl, was then added. Two microliters of RNase (DNase-free, 10 mg/mL) was added and the mixture was incubated for 1 h at 37° C., followed by the addition of Proteinase K (stock=10 mg/mL for a final concentration of 0.5 mg/mL in the mixture). The mixture was then incubated at 37° C. for 2 h. The samples were then extracted with an equal volume of buffer-equilibrated phenol in PhaseLock Gel II Light tubes (5 Prime→3 Prime, catalogue # 5301-171825). Samples were centrifuged at 2000 rpm×5 min. to separate phases and the aqueous top layer was carefully removed and transferred to a new PhaseLock Gel II Light tube. A second extraction was done with an equal volume of buffer-equilibrated phenol/chloroform/isoamyl alcohol (25:24:1) Phase Lock tubes. After centrifuging at 2,000 rpm×5 min., the aqueous layer carefully removed and transferred into a new Phase Lock Tube. An equal volume of equilibrated chloroform/isoamyl alcohol (24:1) in was added. The resulting mixture was centrifuged at 2,000 rpm×5 min. to separate the phases. The aqueous top layer to new tube was placed into a fresh tube and 200 µL 3M sodium acetate (pH, 5.2) one volume isopropyl alcohol was added and the mixture was gently mixed which precipitated the high molecular weight DNA. The precipitated DNA was spooled onto a Pasteur pipette and placed into 250 µL of TE buffer. The samples were dialyzed at 4° C. with two changes of TE buffer. Each genomic DNA sample was quantified on a flourimeter and diluted to 1000 ng in 100 microliters of 0.25×TE buffer for polymerase chain reaction analysis.

EXAMPLE 24

PCR Confirmation of Site-Specific Gene Targeting

The PCR primers were designed to include a primer annealing to the mas promoter and a primer annealing to the luc-int gene. The primers were located in the mannopine synthase promoter were:

5'-TACGCTGACACGCCAAGCCTCGCTA-3' (SEQ ID NO:7);

and in the transcribed region of the luc-int gene:

5'-GTTGCTCTCCAGCGGTTCCATC-3' (SEQ ID NO:8).

A "hot start" PCR procedure using Ampli Wax beads (Perkin Elmer) was used according to the manufacturer's instructions. The lower reaction mixture (25 µL) contained 0.8 mM deoxynucleotide triphosphates, 6 mM $MgCl_2$, 0.4 mM of each oligonucleotide primer, 50 mM KCl, 10 mM Tris-HCl (pH 8.8). The upper reaction mixture (75 µL) contained 50 mM KCl, 10 mM Tris-HCl, pH 8.8, 2.5U Taq Polymerase (Boehringer-Manheim), and 100 ng of genomic DNA in 10 µL of 0.25×TE. Each cycle consisted of 2 min. at 94° C., 2.5 min at 60° C., and 3 min at 72° C. Reactions were terminated following a final extension step of 7 min at 72° C. and 35 cycles.

EXAMPLE 25

DNA Gel Blot Analysis

DNA gel blot analysis was done as described by Allen et al. (*Plant Cell* 5:603–613 (1993)). Agarose (1.25%) gels in TAE buffer were stained with 0.5 µg/mL ethidium bromide and photographed. The gels were then incubated for 45 min in solution containing 0.5 M NaOH and 1.5 M NaCl, rinsed, and then neutralized for 30 and 15 minute washes 1 M TrisCl (pH 8.0) and 1.5 M NaCl. The gels were then blotted to Genescreen (New England Nuclear, Wilmington, Del.) in 10×SSC buffer. The membranes were prehybridized overnight at 42° C. in 20 mL of 50% formamide, 5×SSC, 1×PE, 1 mL Calf liver RNA RNA (625 µg/mL final concentration). Probes were prepared with the multi prime DNA labeling kit from Amersham using gel-isolated luc-inT gene as the template. Washing conditions included two washes at room temperature with 2×SSC, 0.1% SDS for 15 minutes and two washes at 42° C. temperature with 0.5×SSC (1×SSC is 0.15 M NaCl, 0.015 M sodium citrate). Blots were then exposed overnight to X-ray film (Kodak).

EXAMPLE 26

RNA Gel Blots

Cells were collected, as described above for the DNA extractions, and 1.0 to 1.5 g were ground to a fine powder under liquid nitrogen. Two mL of cold RNA extraction buffer was added, followed by the addition 2 mL of Tris-saturated phenol/chloroform solution. RNA extraction buffer contains: 1% SDS, 1 mM aurin tricarboxylic acid (ATA), 1% (w/v) tri-isopropylnapthalene-sulfonic acid (TPNS), 4% (w/v) p-aminosalicylic acid (PAS), 1×TE (10 mM Tris pH 7.5, 1 mM EDTA), 2% (v/v) β-mercaptoethanol (BME). The samples were mixed with a polytron until a homogeneous emulsion was formed. The samples were then centrifuged for 15 min at 10,000 rpm (4° C.) in an RC5B centrifuge (Sorvall). The aqueous phase was placed into 1.5 mL microfuge tubes containing 5 µl of 100 mM ATA. Ten Molar LiCl was then added to then bring final concentration to 1.5 M LiCl. The samples were then mixed and the RNA allowed to precipitate at 4° C. overnight. The samples were then centrifuged in a microfuge (30 min, 13,000 rpm, 4° C.) to pellet the RNA. The RNA pellet was dissolved in 200 µl of 100 µM ATA buffer per sample. One hundred microliters of 100 mM ATA was added to completely dissolve the pellet. For every 100 µL of resuspended pellet, 50 µL of 7.5M $NH_4OAC$ and 300 mL of 95% cold EtOH was added and placed at 20° C. The samples were then centrifuged for 30 min at 13,000 rpm. The pellet was air-dried and the RNA pellet was dissolved in an appropriate amount of 100 µM ATA buffer. The samples were denatured by glyloxylation. 37 µL of glyoxylation buffer was mixed with 30 µg of RNA in 11.0 µL of the 100 mM ATA buffer and incubated at 50° C. for 60 minutes. The glyoxylation buffer contains a ratio of 242 µL glyoxal, 720 µL DMSO, 144 µL 0.1 M $KH_2PO_4$ (pH 7.0).

Five micrograms of RNA were run on each lane in a 1.25% agarose gel in 10 mM $KH_2PO_4$ buffer for 3 to 4 hour and blotted overnight onto GeneScreen™ using 25 mM $KH_2PO_4$ buffer. The membranes were prehybridized overnight at 65° C. in 20 mL of 50% formamide, 5×SSC, 1×PE, 1 mL Calf liver RNA (625 µg/mL final concentration). Probes were prepared using the T3 or T7 RNA polymerase using pGH304, harboring the FLP gene driven by the RNA polymerase promoter, as the template. Washing conditions included two washes at room temperature with 2×SSC, 0.1% SDS for 15 minutes and two washes at 65° C. with 0.5×SSC (1×SSC: 0.15 M NaCl+0.015 M sodium citrate). Blots were then exposed overnight to X-ray film (Kodak).

EXAMPLE 27

PCR Results and Discussion

Figure 5:
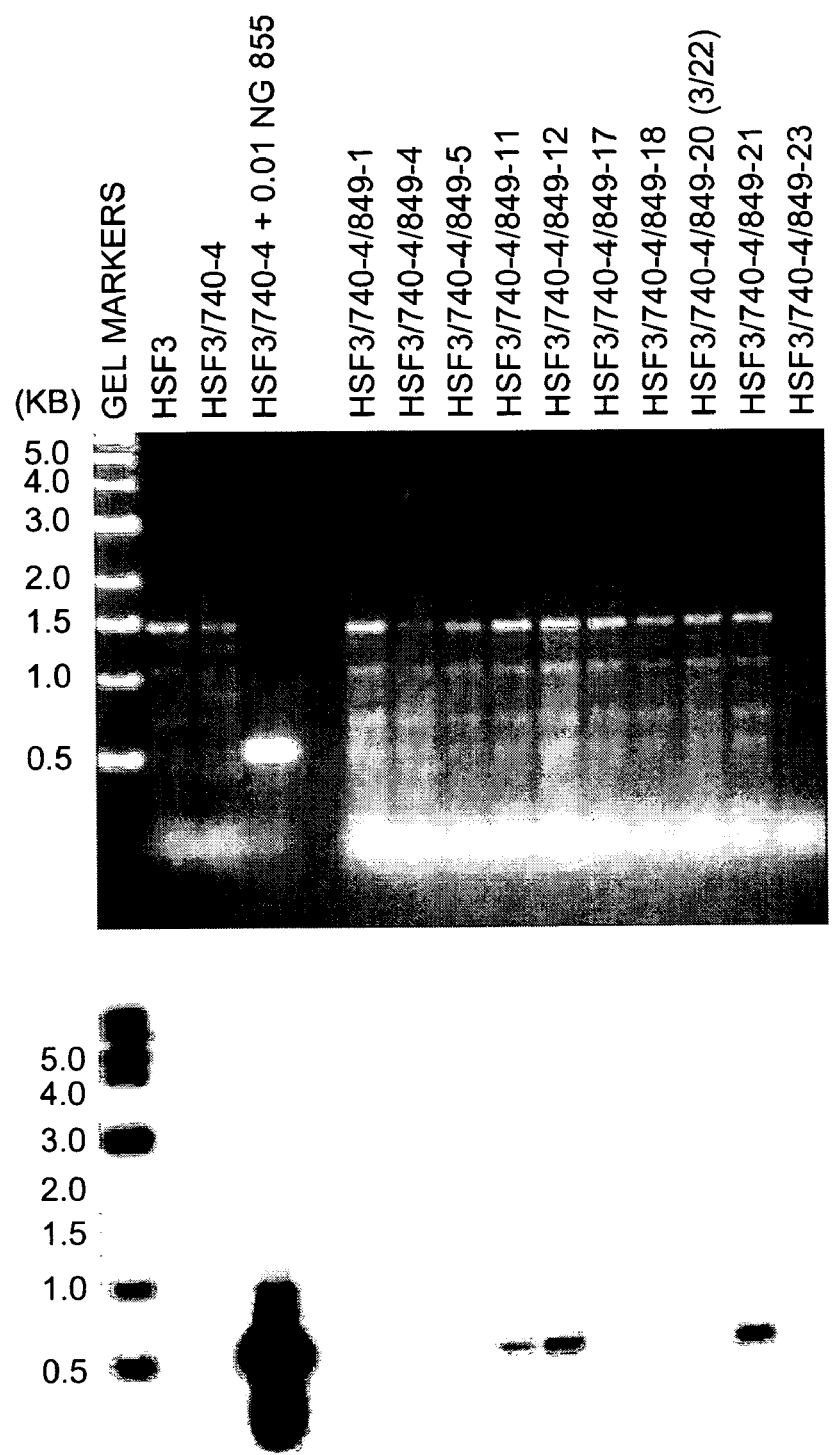
FIG. 5 (See Example 27) illustrates the site-specific gene targeting (GH849) in cultured tobacco cells. NT-1 cells containing a single copy of the GH740 Tag (740-4) and the HS::FLP gene were re-transformed with Agrobacterium vector containing the targeting construct GH849 and selected on 50 µg/mL hygromycin. Isolates were selected and suspension cultures started. The suspension cells were grown at 27° C. and transferred weekly by inoculating 0.5 mL into 5 mL of fresh medium. The DNA used for the PCR reaction was collected from cells 64 days after infection (DAI). PCR conditions were 62° C. annealing for 35 cycles. Twenty microliters of each PCR sample were loaded on each lane. The control containing GH855 contained only 6 microliters. The Southern blots were $^{32}$-P probed with gel-isolated Luc-Int insert from pLUK07 and hybridized at 42° C. The film was exposed overnight at minus 70° C.
Figure 6:
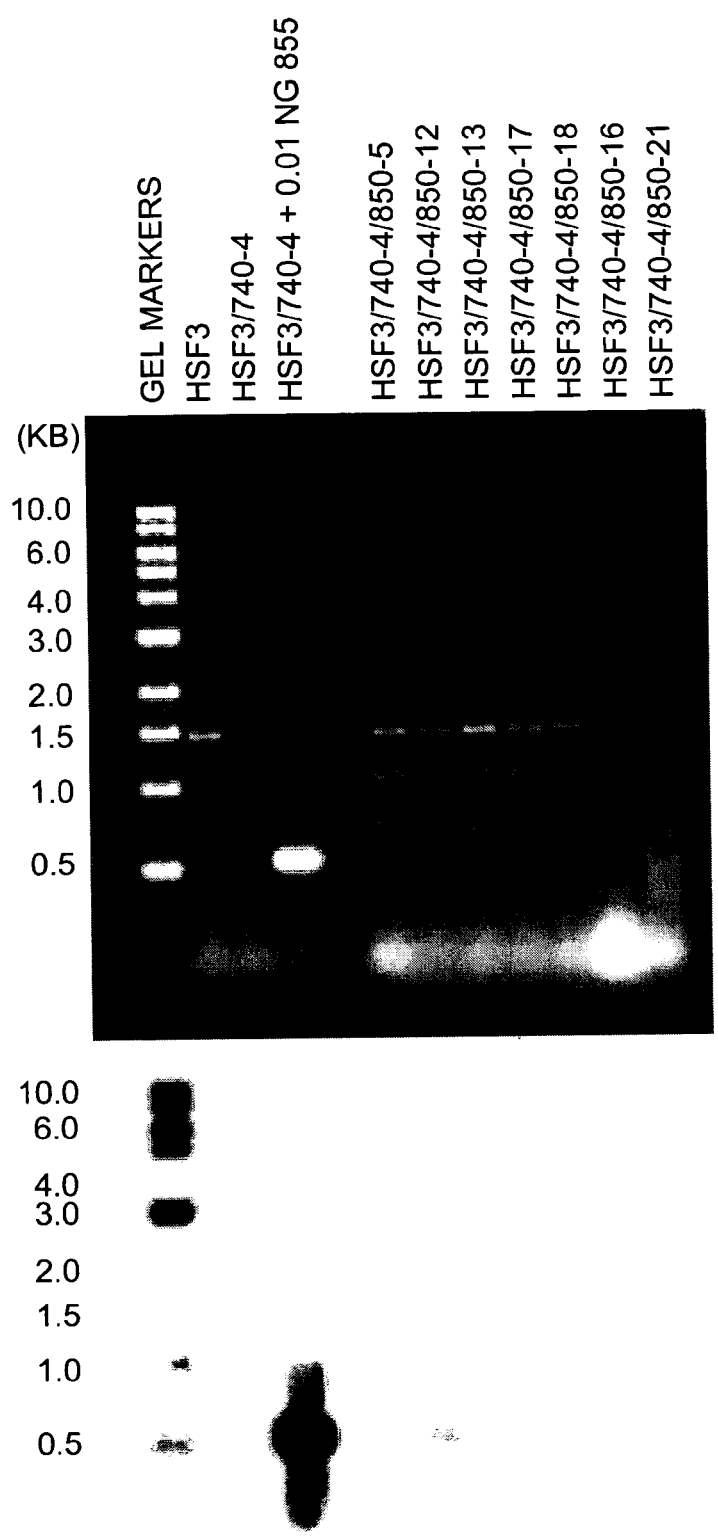
FIG. 6 (See Example 27) illustrates site-specific gene targeting (GH850) in cultured tobacco cells. NT-1 cells containing a single copy of the GH740 Tag (740-4) and the HS::FLP gene were re-transformed using Agrobacterium with the integration targeting construct GH850 and selected on 50 µg/mL hygromycin. Isolates were selected and suspension started. The suspension cells were grown at 27° C. and transferred weekly by inoculating 0.5 mL into 5 mL of fresh data. The DNA used for the PCR reaction was collected from cells 64 days after infection (DAI). PCR conditions were 62° C. annealing for 35 cycles. Twenty microliters of each PCR sample were loaded on each lane. The control containing GH855 contained only 6 microliters. The Southern blots were probed with gel-isolated $^{32}$-P labeled Luc-Int insert from pLUK07 and hybridized at 42° C. The film was exposed overnight at minus 70° C.

DNA was isolated from the Tagged cell line HSF-3/740-4 which had been re-transformed using *Agrobacterium* with either integration targeting construct pGH850 or incoming targeting construct pGH849 (these constructs have been described above). One hundred ng of the genomic DNA was amplified using a "Hot-Start" PCR reaction as described by Allen et al, supra (1993), except that 35 cycles were used with an annealing temperature of 62° C. The primers were designed such that one primer would anneal to the mas promoter (from the genomic Tagged DNA) and the other primer would anneal to the luc-int gene (from the Targeting DNA). FIG. 5 and FIG. 6 show the ethidium bromide-stained gels on the top portion of each panel. The left most lane shows the molecular weight markers. The next two lanes show parental controls for HSF-3 (heat shock Flp line 3) and HSF-3/740-4 (heat shock Flp line 3 re-transformed with the Tag construct pGH740 to produce line 4). The next lane includes the positive control pGH855, [masP-5'-FRT-luc-int-nosT] (0.01 ng DNA) spiked into 100 ng of the chromosomal Tag HSF-3/740-4 genomic DNA. Amplified DNA from the individual lines transformed with the targeting vectors pGH849 or pGH850 is shown in the remainder of the lanes.

The banding pattern on the ethidium-stained gels is inconclusive for the Targeting lines, but shows a strongly staining band for amplified pGH855 DNA. This band was used as the reference for positive targeting. When the blots were probed with a $^{32}$P-labeled luciferase DNA, 4 of 10 (40%) of the lines targeted with GH849 and 3 of 7 (42%) of the lines targeted with GH850 show a band of equal molecular weight to the positive spiked control pGH855. The HSF-3/740-4 lines showing targeting include 849-11, 849-12, 849-20, 849-21, 850-5, 850-6, and 850-13 (which is a very faint band). The DNA from 850-21 shows bands of improper size, suggesting that some rearrangement had occurred in this line.

The pGH849 and pGH850 vectors differ in that only one FRT recombination target site was included in pGH850 (located prior to the luc-int reporter gene). [see FIG. 2 above], whereas in pGH849, two FRT sites flank the luc-int reporter gene [see FIG. 1 above]. Thus one would predict that the positive targeting with pGH850 would differ from that with pGH849; and the resulting genomic chromosomal target site would vary according to whether FLP-mediated recombination at the FRT sites occurred from the *Agrobacterium* T-DNA before the T-DNA insertion into genomic DNA or after T-DNA insertion to the genome.

For pGH849, FLP-recombination at the FRT sites before T-DNA insertion into the genome would be expected to result in the insertion of luc-int into the genomic chromosomal target site, probably via the circular intermediate created by Flp recombinase-catalyzed recombination at the two flanking FRT sites of pGH849. In this case, there most probably would not be other T-DNA sequences transferred to the genome, so it would not be expected that the resulting plant or plant cells would be hygromycin resistant. FLP-mediated recombination at the FRT sites after pGH849 T-DNA insertion into the genome would result in the same kind of luc-int insertion, but would also result in a genomic "footprint". This footprint would include T-DNA borders surrounding T-DNA sequences including a single FRT site and the plant hygromycin resistance gene from the pGH849 T-DNA.

FLP-mediated recombination at the FRT sites before pGH850 T-DNA insertion into the genome would be expected to result in the presence of binary vector sequences at the chromosomal targeting site in the genome. In addition, the hygromycin resistance gene would probably not be present and expressed in the resulting plant cells. FLP-mediated recombination at the FRT sites after insertion of GH850 T-DNA into the genome would be expected to result in hygromycin resistance gene presence and expression. A further result might be a crossover between the chromosome bearing the GH740 tag and that bearing the GH850 luc-int sequences, which would create a chromosomal translocation.

The high frequency of chromosomal gene targeting was also impressive (greater than 40%). It was likely that the frequency could have been even higher, but was limited by the dynamic equilibrium of the two directly repeated FRTs in the presence of leaky Flp recombinase expression (driven by the soybean heat shock promoter). Out of 19 targeting lines tested, all 19 showed luciferase activity. The lines from which DNA was isolated, and subsequently used for the PCR experiment shown in FIG. 5 and FIG. 6, were the same lines tested earlier, except the DNA was isolated after an additional month of growth.

EXAMPLE 28

Tobacco Plant CR500

Figure 7:
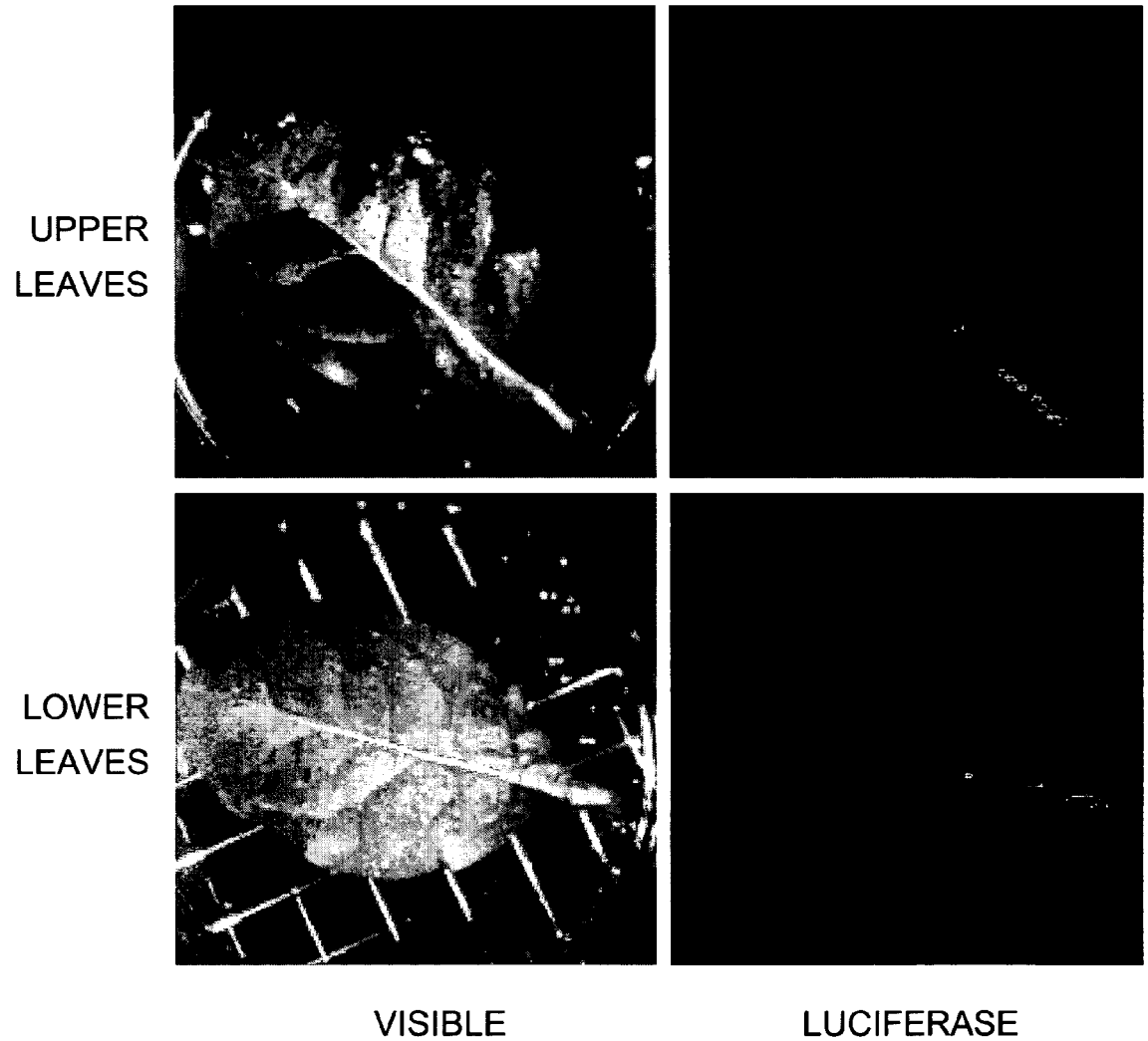
FIG. 7 (See Example 28) illustrates visible light and luciferase luminescence images from a tobacco plant produced by the method of the present invention, taken at the time just before the first flowers opened.

FIG. 7 shows Tobacco Plant CR500 imaged just at the beginning of flowering. The composite shows visible light images on the left panels and photon imaged luciferase on the right panels. Both the upper and the lower side of the leaf were imaged. This leaf was the lowest mature leaf on the plant; concomitantly the uppermost mature leaf was harvested for molecular analysis. The luciferase data was collected after spraying the leaf with 5 mM luciferin. CR500 was the R-0 generation for the incoming promoterless luc-int gene GH849 (the Target), R-1 for GH740 (the Tag), and R-2 for HSP-FLP (Heat-Shock FLP).

The luciferase image shows the transgenic plant leaf clearly expressing luc activity throughout the leaf, with more apparent expression in the veins and vasculature. Because the incoming luc gene has no promoter, luc expression as seen here is evidence for this gene having become operably-linked with a regulatory sequence capable of promoter activity. Therefore this result indicates that the luc gene is probably being expressed from the mas promoter and that a positive targeting event probably occurred early in the development of the tissue from which this plant grew.

Expression from a cryptic promoter cannot be ruled out though; molecular details will confirm the targeting.

Note that this plant developed from tissue which was not subjected to antibiotic selection for the incoming target pGH849.

EXAMPLE 29

Transgenic Plants Having Gene Expression Stabilized via High Efficiency Gene Targeting: Such Stabilization Existing Over Generations First transgenic generation (R-0) plants produced by the High Efficiency Gene Targeting invention of this disclosure have the "new" gene expressed in a consistent, stable, and predictable manner. This consistent, stable, and predictable gene expression is the pattern of expression of the FRT-tagged reporter gene at that chromosomal site. In various independent Tagged lines, such reporter gene expression for example might be 5 units in one line, 10 units for the second line and 15 units in a third line. After High Efficiency Gene Targeting with the same "new" gene into each of these lines, the resulting newly-introduced gene(s) at those particular chromosomal sites shows expression in the ratio of 1:2:3 for the lines corresponding to original line one, two, and three. These lines are then each backcrossed, producing R-1 progeny lines having the same 1:2:3 ratios of gene expression.

EXAMPLE 30

Using this System to Insert Very Large Pieces of DNA at Precise Places in the Genome A construct similar to pGH850 comprised of a single FRT recombination target site in linear proximity to a piece of heterologous DNA (the heterologous DNA being 100 bp in size, but is not a limitation of the system) was used. This construct, pGH850MEGA, was a binary plasmid with the insert of interest in the T-DNA. *Agrobacterium*, bearing pGH850MEGA, were used to transfer this DNA to the plant into which it was inserted. Insertion was facilitated by screening for the appropriate plant drug resistance marker; for example hygromycin resistance. In the presence of FLP recombinase and a chromosomal FRT recombination target site, the large piece of DNA carried by pGH850MEGA was precisely integrated at the chromosomal FRT site.

EXAMPLE 31

Figure 8:
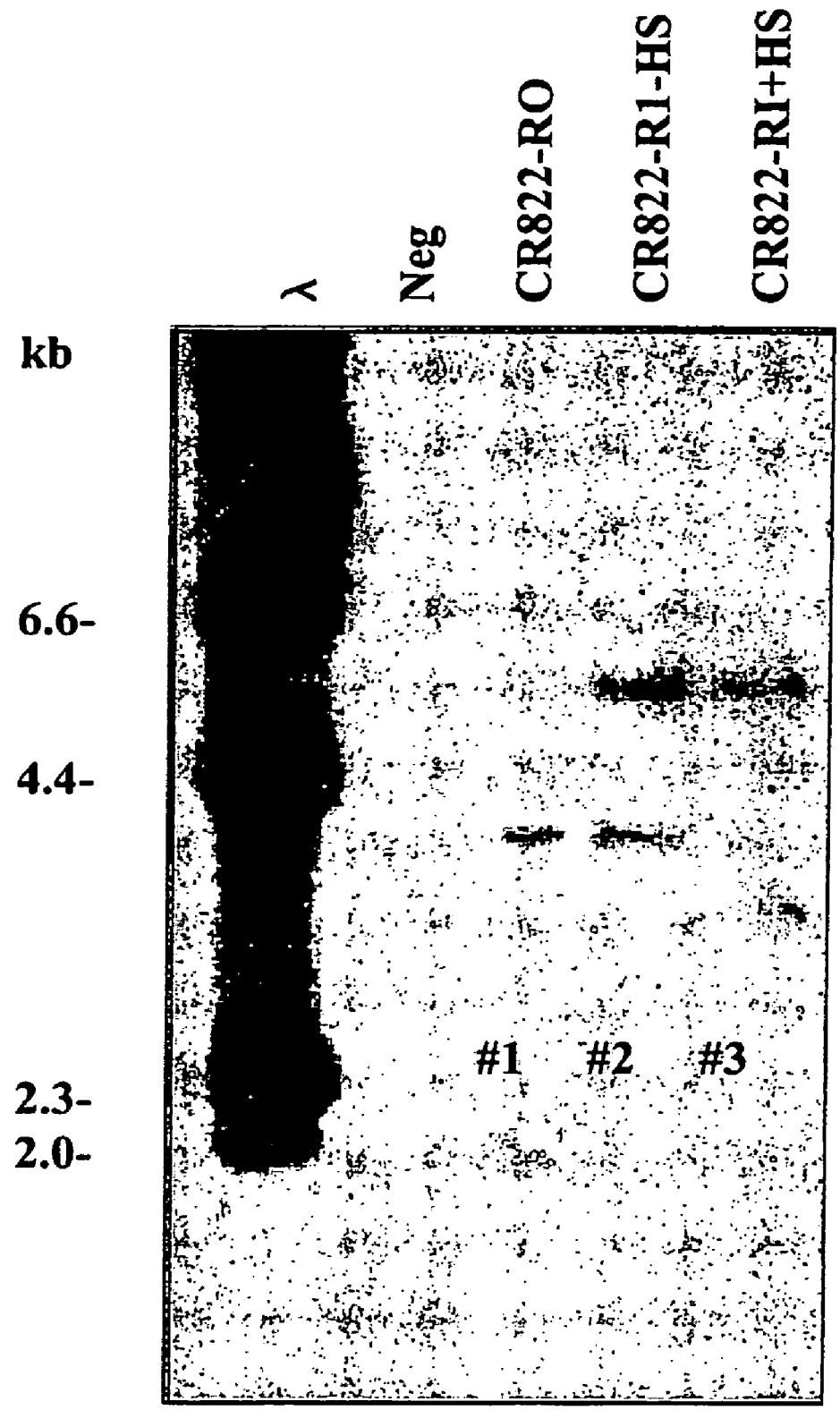
FIG. 8 illustrates genomic Southern analysis of "targeted" tobacco seedlings.

Triple Transgenic Tobacco Plants and Genomic Southern Analysis of R-0 and R-1 Plants Genomic Southern analysis was conducted on site-specific gene targeting with pGH849 in tobacco tissue and seedlings. Leaf disks of plants transgenic for HSP-FLP and GH740 Tag were re-transformed using *Agrobacterium* bearing T-DNA carrying GH849 and tissue selected on 50 mg/L hygromycin. Plants were regenerated, self-pollinated, R-1 seedlings subjected to plus and minus heat-shock (HS) conditions, allowed to recover (Kilby et al, *Plant J.* 8:637–652(1995)) and assayed for luciferase activity. One line, Cr822, showing luc-minus activity before HS and luc+ activity after HS, was subjected to genomic Southern analysis. Genomic DNA digested with ScaI and EcoRI was loaded on lanes #1, 2, and 3 (one μg/lane). Gel blots were probed with gel-isolated luciferase insert (FIG. 8). Lanes #1 (Cr822, R-0 plant), #2 (Cr822 R-1 seedlings-no HS), and #3 (Cr822 R-1 seedlings +HS) show a luc band (3.8-kb) of the parental promoterless luc gene (rightward arrow). R-1 seedlings (lanes #2 & 3) show a larger (5.7-kb) luc band as well (leftward arrow), the size predicted for the targeted insertion of the luc gene into the Tag at the FRT site. Lambda HindIII DNA markers in far left lane (FIG. 8).

EXAMPLE 32

Triple Transgenic Tobacco Plants-Luciferase Phenotypic Analysis of R-0 and R-1 Plants (Plus and Minus HS)

R-1 seedlings of triple transgenic lines were subjected to heat-shock manipulation (Kilby et al) and analyzed for luciferase activity using a photon imager. Of the plant lines receiving pGH849, twenty-two were screened, four of which were phenotypically luc+. Plant line Cr194 was transgenic for HSP-FLP and GH740 Tag. Lines showing desired luciferase phenotype are indicated in Table 1 below.

TABLE 1

Triple Transgenic Plants - Luciferase Phenotypic Analysis.

| Plant Line | transgenes | Luc: R-0/R-1 | GUS Phenotype | Growth Conditions |
|---|---|---|---|---|
| Cr 469 | GH850/Cr194 | luc+/luc+ | 5+ of 5 | R0-HygR/R1 no Sel'n |
| Cr 705 | GH850/Cr194 | luc+/luc+ | 5+ of 6 | R0-HygR/R1 no Sel'n |
| Cr 706 | GH850/Cr194 | luc+/luc+ | 6+ of 6 | R0-HygR/R1 no Sel'n |
| Cr 822 | GH849/Cr194 | luc−/luc+ | 5+ of 6 | R0-HygR/R1 no Sel'n |
| Cr 825 | GH849/Cr194 | luc−/luc+ | 6+ of 6 | R0-HygR/R1 no Sel'n |
| Cr 829 | GH849/Cr194 | luc−/luc+ | 6+ of 6 | R0-HygR/R1 no Sel'n |
| Cr 831 | GH849/Cr194 | luc−/luc+ | 6+ of 6 | R0-HygR/R1 no Sel'n |

EXAMPLE 33

Triple Transgenic Tobacco-Enhanced and "Primed" Plant-*Agrobacterium* Growth and Co-cultivation Conditions Plant tissue leaf disks were "primed" before cultivation with *Agrobacterium* by pre-growing leaf disks on hormone-containing medium (BAP, 10 micromoles/L; NAA, 10 micromole/L; and 2, 4 D, 1 micromoles/L) for 2 days. *Agrobacterium* was pre-induced with Acetosyringone (200 μM) prior to co-cultivation with plant tissue. Leaf disks, which had been co-cultivated with *Agrobacterium*, were grown for a period of time without selecting for the infecting T-DNA marker after killing the *Agrobacterium*. The period of time post *Agrobacterium* killing and without T-DNA marker selection was at least 10 days. These leaf disks were analyzed phenotypically for luc expression and the results are given in Table 2. These results suggest that experimental variables manipulated in this experiment are effective in producing plant tissue phenotypes indicative of gene targeting during early phases of plant growth. In one host line, Cr843, gene targeting, as indicated by positive and high luc activity, is substantial.

TABLE 2

Triple Transgenic Tobacco-Enhanced and "Primed" Plant-*Agrobacterium* conditions. Luciferase Assay of Leaf Disks.

| Host Genotype | T-DNA Intro | Growth Conditions | DaysPost Co-Cult | # disks | luc (cts/2 min) |
|---|---|---|---|---|---|
| Wild-Type cgteriu | Seedlings-NoAgro | NoSel/NoHormones | 3 wks old | 3 small | 615 |
| Cr843 | HSP-FLP | Selection/BarR | 23 | one | 17,374 |
| Cr843 | FLP-1 | Selection/BarR | 23 | one | 30,667 |
| Cr843 | FLP-1 | Selection.BarR | 23 | one | 26,080 |
| Cr843 | FLP-1 | No Selection | 27 | two | 20,680 |
| Cr843 | HSP-FLP | Selection/BarR | 23 | one | 19,643 |
| Cr843 | HSP-FLP | Selection/BarR | 23 | one | 27,536 |
| Cr843 | HSP-FLP | Selection/BarR | 23 | one | 30,307 |
| Cr843 | HSP-FLP | No Selection | 23 | two | 15,847 |
| Cr843 | seedlings-NoAgro | NoSel/NoHormones | 3 wks old | 3 small | 584 |
| Cr751 | FLP-1 | No Selection | 27 | one | 3,617 |
| Cr751 | HSP-FLP | No Selection | 23 | one small | 1,876 |
| Cr751 | HSP-FLP | No Selection | 23 | one small | 5,368 |
| Cr751 | HSP-FLP | Selection/HygR | 27 | one | 1,597 |
| Cr751 | HSP-FLP | Selection/HygR | 27 | one (?) | 1,664 |
| Cr751 | HSP-FLP | Selection/HygR | 27 | one | 876 |
| Cr751 | HSP-FLP | Selection/HygR | 27 | one | 1,750 |
| Cr751 | HSP-FLP | Selection/HygR | 27 | one (?) | 2,526 |
| Cr751 | Seedlings-NoAgro | NoSel/NoHormones | 3 wks old | 3 small | 616 |

Host Genotype - Cr843 bears GH740 in one locus and GH849 in another locus. Cr751 has GH740 in the same locus as Cr843 and GH849 in a locus different from Cr843. GH 740 is the Tag = mas/Frt/GUS; GH849 is the promoterless luc gene flanked by direct repeats of FRT sites.

T-DNA intro - FLP gene on incoming *Agrobacterium* T-DNA; FLP-1 is a CaMV35S-FLP; No *Agrobacterium* is uninfected tissue.

Growth Conditions - No Selection = No plant drug resistance selection; No Hormones = Tissue growing on medium without hormones; Unless otherwise noted all tissue growing with BAP. Selection = plant drug resistance selection, as indicated. Selection was not applied until 10 days after end of co-cultivation.

Days after co-cultivation - days between end of co-cultivation and doing luc assay.

Luc - luciferase activity as analyzed in photon imager using 5 mM luciferin and 2 minute counting time. Numbers are not corrected for background of ~500 c/2 min.

These results indicate that early plant growth conditions as well as *Agrobacterium* growth conditions are important in gene-targeting using this system, and further indicate that further optimization is possible.

The foregoing is illustrative of the present invention, and is not to be construed as limiting thereof. The invention is defined by the following claims, with equivalents of the claims to be included therein.

The invention claimed is:

1. A method for the targeted insertion of a nucleotide of interest into a specific chromosomal site within a plant cell, said method comprising the steps of:
   (a) providing a plant cell having a heterologous target site on a chromosome thereof, wherein said target site is flanked only on one side by a single recombination site, which single recombination site is recognized by a site-specific recombinase enzyme; and then
   (b) transforming said plant cell with an *Agrobacterium* transformation vector carrying a nucleotide sequence of interest, wherein said nucleotide sequence of interest is flanked by a pair of identical recombination sites, one on each side thereof, that correspond to the single recombination site of said target site, so that said nucleotide of interest (i) is randomly inserted into a chromosome of said plant cell, (ii) generates an excision circle therefrom, and then (iii) is inserted into said chromosome at said target site;
   wherein said transforming step is carried out in the presence of a site-specific recombinase effective to carry out recombination at said recombination site and insert said nucleotide of interest into said chromosome at said target site.

2. The method of claim 1, wherein said single heterologous target site is inserted into said chromosome by *Agrobacterium*-mediated transformation.

3. The method of claim 1, wherein said recombinase is an integrase.

4. The method of claim 1, wherein said recombinase is selected from the group consisting of FLP recombinase, Cre recombinase, and recombinase R.

5. The method of claim 1, wherein said recombinase is FLP recombinase, and said recombinase sites are FLP recombination target (FRT) sites.

6. The method of claim 1, wherein said plant cell is a dicot plant cell.

7. The method of claim 1, wherein said plant cell has a genome size greater than 500 megabases.

* * * * *

SEQUENCE LISTING

<160> NUMBER OF SEQ ID NOS: 10

<210> SEQ ID NO 1
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 1
cgactctcga ggaagttcct attccgaagt tcctattctc tag        43

<210> SEQ ID NO 2
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 2
cagatgtcga cgaagttcct atactttcta gagaatagga ac         42

```
<210> SEQ ID NO 3
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 3
cgactggatc cgaagttcct attccgaagt tcctattctc tag                    43

<210> SEQ ID NO 4
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 4
cagaggtacc gaagttccta tactttctag agaataggaa c                      41

<210> SEQ ID NO 5
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 5
gcgcacgcgt aagcttagat ttttcaaatc agtgcgc                           37

<210> SEQ ID NO 6
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 6
gcgcatgcat tctagacgat ttggtgtatc gagattgg                          38

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7
tacgctgaca cgccaagcct cgcta                                        25

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
gttgctctcc agcggttcca tc                                           22

<210> SEQ ID NO 9
<211> LENGTH: 48
<212> TYPE: DNA
<213> ORGANISM: Artificial sequence
<220> FEATURE:
<223> OTHER INFORMATION: FLP recombinase target sequence
```

```
<400> SEQUENCE: 9
gaagttccta tactttctag agaataggaa cttcggaata ggaacttc                48

<210> SEQ ID NO 10
<211> LENGTH: 48
<212> TYPE: DNA
<213> ORGANISM: Artificial sequence
<220> FEATURE:
<223> OTHER INFORMATION: FLP recombinase target sequence complementary
      strand

<400> SEQUENCE: 10
gaagttccta ttccgaagtt cctattagag agaaagtata ggaacttc                48
```